(12) United States Patent
Smith et al.

(10) Patent No.: US 6,310,072 B1
(45) Date of Patent: Oct. 30, 2001

(54) PRODUCTION OF ANALGESIC SYNERGY BY CO-ADMINISTRATION OF SUB-ANALGESIC DOSES OF A MU OPIOID AGONIST AND A KAPPA-2 OPIOID AGONIST

(75) Inventors: Maree Smith, Bardon; Fraser Ross, Clayfield, both of (AU)

(73) Assignees: The University of Queensland, Queensland; The Lynx Project Limited, Australian Capital Territory, both of (AU)

( * ) Notice: Subject to any disclaimer, the term of this patent is extended or adjusted under 35 U.S.C. 154(b) by 0 days.

(21) Appl. No.: 08/921,187

(22) Filed: Aug. 29, 1997

Related U.S. Application Data

(63) Continuation of application No. PCT/AU96/00656, filed on Oct. 21, 1996.

(30) Foreign Application Priority Data

Oct. 19, 1995 (AU) ................................................ PN 6038

(51) Int. Cl.$^7$ ...................... A61K 31/485; A61K 31/454; A61K 31/4535; A61K 31/4468
(52) U.S. Cl. ........................... 514/282; 514/326; 514/329
(58) Field of Search ..................................... 514/282, 326, 514/329

(56) References Cited

FOREIGN PATENT DOCUMENTS

| AU-A-29679/92 | 7/1993 | (AU) . |
| AU-A-30024/92 | 7/1993 | (AU) . |
| AU-A-66058/94 | 1/1995 | (AU) . |
| WO 95/27482 | 10/1995 | (WO) . |

OTHER PUBLICATIONS

Sutters et al., Brain Research, 530, 290–294, 1990.*

* cited by examiner

Primary Examiner—Phyllis G. Spivack
(74) Attorney, Agent, or Firm—Akin, Gump, Strauss, Hauer & Feld, L.L.P.

(57) ABSTRACT

An analgesic composition is disclosed comprising a sub-analgesic dosage of a $\mu$-opioid agonist, optionally in the form of a pharmaceutically acceptable salt, and a sub-analgesic dosage of a $\kappa_2$-opioid agonist, optionally in the form of a pharmaceutically acceptable salt. There is also disclosed a method for producing analgesia in humans and lower animals which comprises administering concurrently to a human or lower animal in need of such treatment an analgesic composition of the invention.

155 Claims, 18 Drawing Sheets

PRODUCTION OF ANALGESIC SYNERGY BY CO-ADMINISTRATION OF SUB-ANALGESIC DOSES OF A MU OPIOID AGONIST AND A KAPPA-2 OPIOID AGONIST

The instant application is a continuation-in-part of Applicants' co-pending International application, Serial Number PCT/AU96/00656, filed Oct. 21, 1996, entitled "PRODUCTION OF ANALGESIC SYNERGY BY CO-ADMINISTRATION OF SUB-ANALGESIC DOSES OF A MU OPIOID AGONIST AND A KAPPA-2 OPIOID AGONIST."

BACKGROUND OF THE INVENTION

1. Technical Field

This invention relates to opioids, and in particular co-administration of sub-analgesic doses of a $\mu$-opioid agonist and a $\kappa_2$-opioid agonist for the production of analgesic synergy.

2. Background Art

Opioid analgesics such as morphine, hydromorphone, oxycodone and fentanyl are among the most powerfully acting and clinically useful drugs producing depression of the central nervous system. These analgesics are the mainstay for the treatment of moderate to severe cancer pain because they are simple to administer and they provide effective pain relief in most patients when used properly (Cancer Pain Relief, World Health Organization, 1986, Geneva).

Unlike doses of non-opioid drugs, weak opioids and mixed opioid agonist-antagonists (e.g., buprenorphine), the doses of morphine and other strong opioids can be increased indefinitely, being limited only by the development of unacceptable side effects. These side effects include the development of physical dependence and tolerance, sedation, respiratory depression, hypotension, increase in cerebrospinal fluid pressure, nausea, vomiting and constipation.

In some patients, particularly the chronically ill, the opioid side effects make it impossible to administer dosages sufficient to adequately control pain over the required time period. Therefore, more active analgesic combinations are in constant demand which offer the possibility of relieving pain with reduced dosages to thereby diminish the expected side effects and toxicity that might result from the otherwise required higher dosages.

In order to explain the above dichotomous effects, it has been postulated (U.S. Pat. No. 5,512,578) that strong opioids such as morphine are bimodally-acting in that they activate both inhibitory and excitatory opioid receptor-mediated functions of neurones in the nociceptive pathways of the nervous system. In this regard, the inhibitory receptors are considered to be responsible for the production of analgesia and the excitatory receptors are regarded to be involved in the production of some of the undesirable side effects referred to above.

Morphine remains the most widely used analgesic for treatment of moderate to severe pain and is the gold standard against which all opioids are compared. In an effort to make morphine of greater use in the treatment of pain, it has been combined with a variety of substances intended to inhibit one or more of its undesirable side effects. To this end, reference may be made to U.S. Pat. No. 2,770,569 which is directed to a combination of morphine with the compound levo-d-hydroxy-N-allyl-morphinan which is said to suppress or eliminate such undesirable side reactions of morphine as respiratory depression, nausea and vomiting.

Reference also may be made to U.S. Pat. No. 4,126,684 which discloses a reduction of either the addiction liability of an addictive substance such as a narcotic analgesic or a barbiturate or the withdrawal symptoms caused by deprivation of such a substance in an addicted subject by administering the addictive substance, e.g., morphine with a 4-amino-3-p-halophenylbutyric acid. In U.S. Pat. No. 4,415,871, reference is made to the prevention of treatment tolerance and physical dependence in chronic morphine treatment by combining the morphine with any of the specific dipeptides indicated therein.

In U.S. Pat. No. 5,041,446 there is disclosed a method of inhibiting the development of tolerance to morphine by combining the morphine with dapiprazole.

In U.S. Pat. No. 5,057,519 there is described a reduction in morphine tolerance by combining the morphine with a benzamide antagonist for a sub-type of the serotonin receptor, $5\text{-}HT_3$.

Reference also may be made to U.S. Pat. No. 5,321,019 in which is disclosed a composition containing an addictive substance such as morphine or codeine and at least one non-toxic substance that blocks the N-methyl-D-aspartate (NMDA) receptor which inhibits the development of tolerance to and/or dependence on the addictive substance.

In addition to morphine, other strong opioids have been combined with a variety of substances intended to alleviate one or more of their undesirable side effects. To this end, reference may be made to U.S. Pat. No. 4.569,937 which is directed to pharmaceutical compositions of ibuprofen and narcotic analgesics such as oxycodone, oxymorphone, hydrocodone, hydromorphone, morphine, meperidine, and methadone. These compositions were found to exhibit unexpected synergism enabling the use of lower doses of either or both drugs with a concomitant reduction in risk of possible side effects.

Reference also may be made to U.S. Pat. No. 4,769,372 which describes a method for treating chronic pain or chronic cough in a patient while preventing or alleviating the development of constipation or other symptoms of intestinal hypomotility wherein an opioid analgesic or antitussive such as morphine, meperidine, oxycodone, hydromorphone, codeine and hydrocodone is administered to the patient together with an opioid antagonist such as naloxone, naloxone glucuronide and nalmefene glucuronide. However successful this therapeutic combination may be in inhibiting the development of constipation or other symptoms of intestinal hypomotility, it does not address the problems of tolerance and/or dependence that are associated with the long term administration of narcotic analgesics.

In Australian Patent Application 88042/82 reference is made to an analgesic composition comprising an analgesic effective amount of a narcotic analgesic selected from the group consisting of morphine, oxymorphone, oxycodone and hydromorphone and an analgesic effective amount of nalbuphine. These combinations are said to improve analgesia while reducing or eliminating the respiratory depression and euphoria usually associated with narcotics.

Reference also may be made to European Patent Application Publication No. 0080047 which discloses combinations of a strong opioid such as morphine or oxycodone with the carbazole compound 6-chloro-$\alpha$-methyl-carbazole-2-acetic acid. This carbazole compound is said to potentiate the analgesic action of morphine or oxycodone, thereby reducing the amount of opioid used.

In U.S. Pat. No. 5,317,022 there is disclosed a composition for the selective blockade of opioid binding sites of the brain responsible for respiratory depression comprising an analgesic effective amount of a codeine derivative and in a mass ratio of 1:2–3 morphine or a morphine derivative indicated therein.

Reference also may be made to U.S. Pat. No. 5,512,578 which is directed to a method for selectively enhancing the analgesic potency (inhibitory effects) of a bimodally-acting opioid agonist such as morphine and simultaneously attenuating the undesirable side effects (excitatory effects) caused by chronic administration thereof comprising co-administration of the bimodally-acting opioid agonist and an opioid receptor antagonist which selectively inactivates excitatory opioid receptor-mediated side effects. Accordingly, this mode of analgesia is purported to be effected by co-administration of two opioid compounds, one of which binds to and acts as a selective agonist at inhibitory opioid receptors to cause analgesia and the other of which binds to and acts as a selective antagonist at excitatory opioid receptors so as to attenuate undesirable side effects caused by the administration of the bimodally-acting opioid agonist while simultaneously enhancing the analgesic effects thereof. In particular, the studies disclosed in U.S. Pat. No. 5,512,578 showed that in cultured fetal dorsal root ganglion sensory neurones co administration of conventional concentrations ($\mu$M) of bimodally-acting opioid agonists such as morphine with ultra-low concentrations (fM-pM) of opioid receptor antagonists such as naloxone, naltrexone, diprenorphine, etorphine and dihydroetorphine resulted in a marked shortening of the action potential duration (APD) which is consistent with markedly enhanced inhibitory effects.

It is a commonly held view (Mather, L. E., 1995, Clin. Exp. Pharmacol. Physiol., 22, 833–836) that all clinically used opioid drugs including hydromorphone, oxycodone and fentanyl mediate their analgesic/antinociceptive effects in the same manner as morphine; i.e., by interacting with $\mu$-opioid receptors in the CNS To this extent, recent years have seen the development of novel opioid analgesics acting through receptors distinct from those utilized by morphine. Three major types of opioid receptors have been pharmacologically defined, namely $\mu$, $\delta$, and $\kappa$, and these are further subdivided into various subtypes (for a review see Pastemak, G. W., 1993, Pharmacological Mechanisms of Opioid Analgesics In Clin. Neuropharmacol., 16, 1–18). It has been suggested that since the effects of endogenous opioids are mediated by at least these three different receptor types, highly selective exogenous opioid agonist or antagonist ligands might have therapeutic applications (Martin, W. R., 1983, Pharmacol. Rev., 35, 283). Thus, if a ligand acts at a single opioid receptor type or sub-type, the potential side effects mediated through other opioid receptor types can potentially be minimised or eliminated.

In this regard, reference may be made to U.S. Pat. No. 5,352,680 which is directed to a therapeutic method for treating opioid tolerance comprising administering a $\delta$-opioid receptor antagonist to block or reduce the tolerance of an opioid $\mu$-receptor agonist such as morphine.

Reference also may be made to U.S. Pat. No. 5,319,087 which discloses the blocking of the $\mu$ or $\kappa$ receptors in the brain using trans-3,4-1-substituted-3-substituted-4-methyl-4-(3-substituted phenyl)-piperidines as opioid antagonists.

Several studies have demonstrated that combinations of $\mu$- and $\delta$-agonists, administered intrathecally, produce enhanced analgesic effects or analgesic synergy (i.e., more than additive analgesic effects) (Larson et al., 1980, Eur. J. Pharmacol., 61, 381–383; Roerig & Fugimoto, 1989, J. Pharmacol. Exp. Ther. 249, 762–768). Other studies have shown that simultaneous intrathecal administration of combinations of a selective $\mu$-opioid agonist (DAMGO) with both a $\kappa_1$-selective (U50,488H) or a $\delta$-selective (DPDPE) opioid agonist also produce analgesic synergy (Miaskowski et al., 1990, Brain Research, 509, 165–168) in addition, potent analgesic synergy has been observed with combinations of a low-analgesic dose of a selective $\mu$-agonist (DAMGO) co-administered into the central nervous system (CNS) with sequentially increasing doses of either a selective $\delta$-(DPDPE) or a selective $\kappa_1$-agonist (U50,488H) (Sutters et al., 1990, Brain Research, 530, 290–294).

These studies demonstrate that all three major classes of opioid receptors can interact to produce antinociceptive synergy. However, the magnitude of the interactions vary markedly depending on which combinations of selective opioid receptor agonists are administered. The data from these studies demonstrate that co-activation of the $\mu$-opioid receptor, with either $\delta$- or $\kappa_1$-opioid receptors, results in the largest enhancement in antinociceptive effects. Importantly, these marked enhancements in antinociception are not attributable to increases in motor deficits.

From the foregoing, a number of non-toxic substances have been defined which may ameliorate some of the undesirable side effects resulting from prolonged administration of strong opioids. In addition, combinations of experimental substances have been defined including $\mu$-, $\kappa_1$- and $\delta$-agonists which result in a synergistic increase in analgesia.

None of these references, however, suggest in any way the desirability of concurrent administration of two strong opioids for analgesic synergy and/or amelioration of their respective undesirable side effects. In fact, just the opposite is suggested. For example, in the World Health Organization's (WHO) guidelines for the relief of cancer pain (Cancer Pain Relief, 1986, supra), it is recommended that co-administration of two strong opicids should never be attempted. Instead, it is recommended that an analgesic ladder should be followed wherein a non-opioid drug is administered initially to a patient and when pain persists or increases, a weak opioid is added to the medication. When the weak opioid drug in combination with the non-opioid drug fails to relieve the pain, a strong opioid is then administered in place of the weak opioid drug. Importantly, it is stipulated that only one opioid drug should be given at any one time.

The current invention arises from the unexpected discovery that co-administration of sub-analgesic dosages of two strong opioids such as morphine and oxycodone results in potent analgesic synergy and a reduced propensity for causing the undesirable side effects herein described. It was further found that oxycodone is a $\kappa_2$-opioid agonist and that co-administration of a sub-analgesic dosage of a $\kappa_2$-opioid agonist with a sub-analgesic dosage of a $\mu$-opioid agonist also results in strong analgesic synergy with reduced undesirable side effects.

OBJECT OF THE INVENTION

It is therefore an object of the present invention to provide an analgesic composition having high analgesic potency and a reduced propensity for causing undesirable side effects by acute and chronic administration thereof.

It is also an object of the invention to provide a method for producing analgesia in humans and lower animals in which some of the undesirable effects of acute and chronic administration of strong opioids are substantially attenuated.

SUMMARY OF THE INVENTION

According to one aspect of the invention there is provided an analgesic composition comprising a sub-analgesic dosage of a μ-opioid agonist suitably in the form of a pharmaceutically acceptable salt and a sub-analgesic dosage of a $κ_2$-opioid agonist suitably in the form of a pharmaceutically acceptable salt.

The term "μ-opioid agonist" as used herein refers to a substance which activates a μ-opioid receptor.

The μ-opioid agonist may be selected from the group including morphine, fentanyl, sufentanil, alfentanil and hydromorphone inclusive of analogs or derivatives thereof. Preferably, the μ-opioid agonist is morphine or analog or derivative thereof.

For the purposes of this invention, the term "$κ_2$-opioid agonist" as used herein refers to selective κ-opioid receptor agonists wherein the antinociceptive effects thereof are substantially attenuated by nor-BNI (nor-binaltorphimine; a putatively selective $κ_1/κ_2$-opioid receptor ligand) and wherein the binding thereof to rat brain membranes is not substantially displaceable by the $κ_1$-selective ligand U69, 593. Preferably, the $κ_2$-opioid agonist is oxycodone.

Of course it will be appreciated that a sub-analgesic dosage of an opioid agonist having dual selectivity for both μ and $κ_2$ receptors may not be expected to synergize with a sub-analgesic dosage of another μ- or $κ_2$-opioid agonist because such dual selective ligand may bind to each of the above receptors which may result in lack of occupancy of said other μ- or $κ_2$-opioid agonist to its selective receptor.

The term "pharmaceutically acceptable salt" as used herein refers to a salt which is toxicologically safe for human and animal administration. This salt may be selected from a group including hydrochlorides, hydrobromides, hydroiodides, sulphates, bisulphates, nitrates, citrates, tartrates, bitartrates, phosphates, malates, maleates, napsylates, fumarates, succinates, acetates, terephthalates, pamoates and pectinates.

Preferably, the pharmaceutically acceptable salt of oxycodone is a hydrochloride, a terephthalate or a pectinate.

Suitably, the pharmaceutically acceptable salt of morphine is a hydrochloride, a sulphate or a tartrate.

The term "sub-analgesic dosage" as used herein refers to a dosage of a μ-opioid agonist solus or a $κ_2$-opioid agonist solus which dosage does not result in the production of analgesia when administered to a human or antinociception when administered to a lower animal requiring alleviation of pain. To this extent, it is well known that the lower threshold for an initial dosage of morphine which results in production of analgesia in a naive human adult is 30 mg every four hours administrable by the oral route (Cherny and Portenoy, entitled "Practical Issues In The Management of Cancer Pain" In "Textbook of Cancer Pain", Third Edition, Eds. Wall and Melzack, Churchill Livingstone) and 4–5 mg every four hours administrable by the intravenous route (Twycross, R. G., entitled "Opioids" In "Textbook of Cancer Pain", Third Edition, Eds. Wall and Melzack, Churchill Livingstone, pp 943–962). Reference also may be made to an article by Beaver et al. (1978, *J. Pharmacol. Exp. Ther.* 207:92–100) which specifies that the lower threshold for an initial dosage of oxycodone resulting in production of analgesia in a naive human adult is 10 mg every four hours administrable by the oral route. Accordingly, the term "sub-analgesic dosage" includes within its scope dosages falling below such lower thresholds. This term will also cover direct administration of the μ- or $κ_2$-opioid agonist as well as administration which includes controlled-release of the μ- or $κ_2$-opioid agonist as described herein after. Of course it will be appreciated that a sub-analgesic dosage of a μ- or $κ_2$-opioid agonist in accordance with the invention will be dependent upon the mode or route of administration thereof.

Suitable sub-analgesic dosages of such opioid agonists may be readily determined by those of skill in the art. For example, in the case wherein the μ-opioid agonist comprises morphine or analog or derivative or pharmaceutically acceptable salts thereof, an initial sub-analgesic dosage of such agonist for a human adult through an intracerebroventricular route may be between about 0.05 mg and about 0.25 mg per day. It will be appreciated that this dosage may be administered in immediate release or controlled-release forms. For example, controlled-release dosage forms as described hereinafter may be administered every 12 or 24 hours comprising respectively about 3 or 6 times the four hourly dosage given above. In this regard, it is well known that the change from immediate release dosages to controlled release dosages of an opioid is a milligram to milligram conversion which results in the same total 'around-the-clock' dose of the opioid (Cherny and Portenoy, "Practical Issues In The Management of Cancer Pain" In "Textbook of Cancer Pain", Third Edition, Eds. Wall and Melzack, Churchill Livingstone).

An initial sub-analgesic dosage of morphine or analog or derivative or pharmaceutically acceptable salts thereof for a naive human adult through a subcutaneous, intravenous, intramuscular, buccal or sublingual route may be between about 0.5 mg and about 3.5 mg, preferably between about 0.5 mg and about 3.0 mg, more preferably between about 0.5 mg and about 2.5 mg, and most preferably between about 0.5 mg and about 2.0 mg every four hours. Alternatively, in controlled-release dosage form, the initial sub-analgesic dosage may be between about 1.5 mg and about 10.5 mg, preferably between about 1.5 mg and about 9.0 mg, more preferably between about 1.5 mg and about 7.5 mg and most preferably between about 1.5 mg and about 6.0 mg every 12 hours, or between about 3.0 mg and about 21.0 mg, preferably between about 3.0 mg and about 18.0 mg, more preferably between about 3.0 mg and about 15 mg and most preferably between about 3.0 mg and about 12.0 mg every 24 hours.

Suitably, an initial sub-analgesic dosage of morphine or analog or derivative or pharmaceutically acceptable salts thereof for a naive human adult through an oral or rectal route is between about 2.0 mg and about 25.0 mg, preferably between about 5.0 mg and about 20.0 mg, more preferably between about 5.0 and about 15 mg every four hours. Alternatively, in controlled-release dosage form, the initial sub-analgesic dosage may be between about 6.0 mg and about 75.0 mg, preferably between about 15.0 mg and about 60.0 mg, more preferably between about 15.0 mg and about 45.0 mg every 12 hours, or between about 12.0 mg and about 150.0 mg, preferably between about 30.0 mg and about 120.0 mg, more preferably between about 30.0 mg and about 90.0 mg every 24 hours.

An initial sub-analgesic dosage of morphine or analog or derivative or pharmaceutically acceptable salts thereof for a human child through an intracerebroventricular route may be between about 0.05 mg and about 0.25 mg per day.

Suitably, an initial sub-analgesic dosage of morphine or analog or derivative or pharmaceutically acceptable salts thereof for a naive human child through a subcutaneous route is between about 0.01 mg/kg and about 0.09 mg/kg every four hours.

An initial sub-analgesic dosage of morphine or analog or derivative or pharmaceutically acceptable salts thereof for a naive human child through an intravenous route may be between about 0.01 mg/kg and about 0.04 mg/kg every four hours.

Alternatively, an initial sub-analgesic dosage of morphine or analog or derivative or pharmaceutically acceptable salts thereof for a naive human child through an oral or rectal route may be between about 0.1 mg/kg and about 0.4 mg/kg every four hours.

Suitably, an initial sub-analgesic dosage of morphine or analog or derivative or pharmaceutically acceptable salts thereof for a naive lower animal through an oral or parenteral route is between about 0.5 mg/kg and about 5 mg/kg every three to six hours.

In the case wherein the $\kappa_2$-opioid agonist comprises oxycodone or analog or derivative or pharmaceutically acceptable salts thereof, a suitable initial sub-analgesic dosage of such agonist for a human adult through an intracerebroventricular route may be between about 0.05 mg and about 0.25 mg per day.

An initial sub-analgesic dosage of oxycodone or analog or derivative or pharmaceutically acceptable salts thereof for a naive human adult through a subcutaneous or intravenous route may be between about 1.0 mg and about 8.0 mg, preferably between about 1.0 mg and about 6.0 mg, more preferably between about 1.0 and about 4.0 mg every four hours. Alternatively, in controlled-release dosage form, the initial sub-analgesic dosage may be between about 3.0 mg and about 24.0 mg, preferably between about 3.0 mg and about 18.0 mg, more preferably between about 3.0 mg and about 12.0 mg every 12 hours, or between about 6.0 mg and about 48.0 mg, preferably between about 6.0 mg and about 36.0 mg, more preferably between about 6.0 mg and about 24.0 mg every 24 hours.

Suitably, an initial sub-analgesic dosage of oxycodone or analog or derivative or pharmaceutically acceptable salts thereof for a naive human adult through an oral or rectal route is between about 1.0 mg and about 8.0 mg, preferably between about 1.0 mg and about 6.0 mg, more preferably between about 1.0 and about 4.0 mg every four hours. Alternatively, in controlled-release dosage form, the initial sub-analgesic dosage may be between about 3.0 mg and about 24.0 mg, preferably between about 3.0 mg and about 18.0 mg, more preferably between about 3.0 mg and about 12.0 mg every 12 hours, or between about 6.0 mg and about 48.0 mg, preferably between about 6.0 mg and about 36.0 mg, more preferably between about 6.0 mg and about 24.0 mg every 24 hours.

An initial sub-analgesic dosage of oxycodone or analog or derivative or pharmaceutically acceptable salts thereof for a human child through an intracerebroventricular route may be between about 0.05 mg and about 0.25 mg per day.

Suitably, an initial sub-analgesic dosage of oxycodone or analog or derivative or pharmaceutically acceptable salts thereof for a naive human child through a subcutaneous or intravenous route is between about 0.01 mg/kg and about 0.08 mg/kg, preferably between about 0.01 mg/kg and about 0.06 mg/kg, more preferably between about 0.01 mg/kg and about 0.04 mg/kg every four hours. Alternatively, in controlled-release dosage form, the initial sub-analgesic dosage may be between about 0.03 mg and about 0.24 mg, preferably between about 0.03 mg and about 0.18 mg, more preferably between about 0.03 mg and about 0.12 mg every 12 hours, or between about 0.06 mg and about 0.48 mg, preferably between about 0.06 mg and about 0.36 mg, more preferably between about 0.06 mg and about 0.24 mg every 24 hours.

Suitably, an initial sub-analgesic dosage of oxycodone or analog or derivative or pharmaceutically acceptable salts thereof for a naive human child through an oral or rectal route is between about 0.01 mg/kg and about 0.08 mg/kg, preferably between about 0.02 mg/kg and about 0.06 mg/kg, more preferably between about 0.02 mg/kg and about 0.04 mg/kg per day. Alternatively, in controlled-release dosage form, the initial sub-analgesic dosage may be between about 0.03 mg and about 0.24 mg, preferably between about 0.06 mg and about 0.18 mg, more preferably between about 0.06 mg and about 0.12 mg every 12 hours, or between about 0.06 mg and about 0.48 mg, preferably between about 0.12 mg and about 0.36 mg, more preferably between about 0.12 mg and about 0.24 mg every 24 hours.

Suitably, an initial sub-analgesic dosage of oxycodone or analog or derivative or pharmaceutically acceptable salts thereof for a naive lower animal through an oral or parenteral route is between about 0.1 mg/kg and about 5 mg/kg every three to six hours.

According to another aspect of the invention there is provided a method for producing analgesia in humans and lower animals which comprises administering concurrently to a human or lower animal in need of such treatment a composition comprising a sub-analgesic dosage of a $\mu$-opioid agonist suitably in the form of a pharmaceutically acceptable salt and a sub-analgesic dosage of a $\kappa_2$-opioid agonist suitably in the form of a pharmaceutically acceptable salt.

The term "administration concurrently" refers to the administration of a single composition containing both $\mu$- and $\kappa_2$-optoid agonists. or the administration of each such opioid agonists as separate compositions and/or delivered by separate routes within a short enough period of time that the effective result is equivalent to that obtained when both such opioid agonists are administered as a single composition.

Any suitable route of administration may be employed for providing a human or lower animal the composition of the invention For example, oral, rectal, parenteral, sublingual, buccal, intravenous, intraarticular, intramuscular, intradermal, subcutaneous, inhalational, intraocular, intraperitoneal, intracerebroventricular, transdermal and the like may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the strong opioids may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutically-acceptable carriers for systemic administration may also be incorporated into the compositions of this invention.

By "pharmaceutically-acceptable carrier" is meant a solid or liquid filler, diluent or encapsulating substance which may be safely used in systemic administration. Depending upon the particular route of administration, a variety of pharmaceutically-acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Pharmaceutical compositions of the present invention suitable for oral or parenteral administration may be presented as discrete units such as capsules, sachets or tablets each containing a pre-determined amount of each of the strong opioids, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the sub-analgesic dosages of each of the strong opioids as described above with the carrier which constitutes one or more necessary ingredients. In general, the compositions are prepared by uniformly and intimately admixing the strong opioids with liquid carriers or finely divided solid carriers or both, and then, if necessary, shaping the product into the desired presentation.

BRIEF DESCRIPTION OF THE DRAWINGS

In order that the invention may be readily understood and put into practical effect, particular preferred embodiments will now be described by way of example with reference to the accompanying drawings in which.

EXAMPLE 1

Figure 1A:
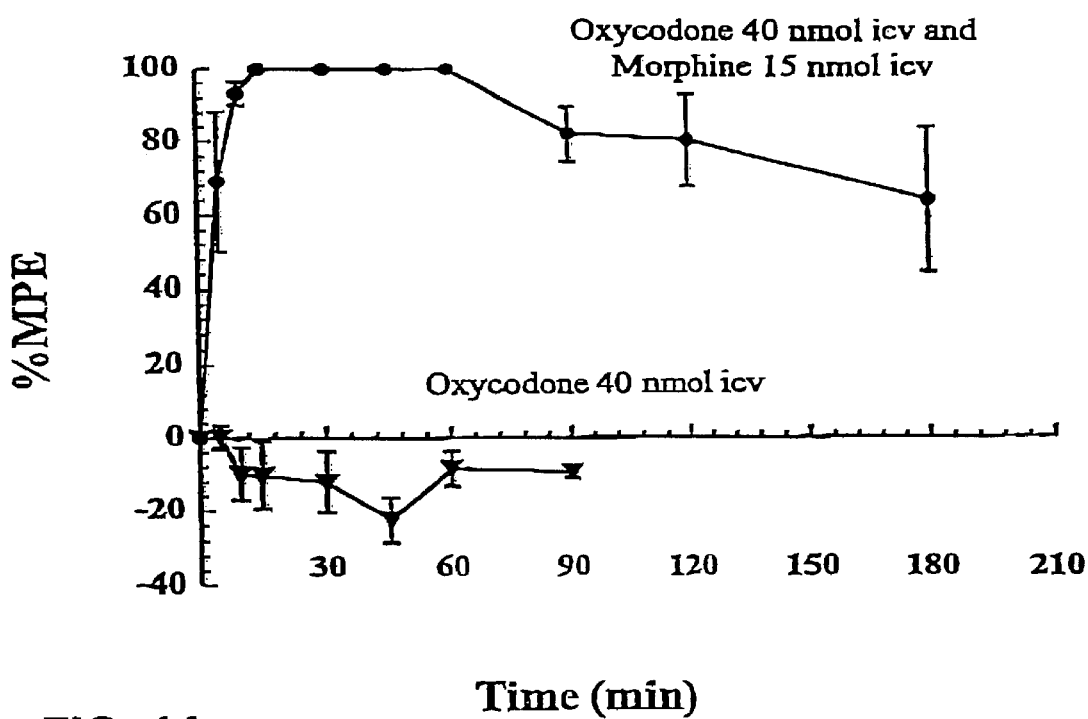
FIG. 1 shows the degree of antinociception (%MPE) as a function of time following i.c.v. administration to Sprague-Dawley rats of: 40 nmol oxycodone in combination with 15 nmol morphine; 40 nmol oxycodone solus; and 15 nmol morphine solus.

Co-administration of Oxycodone and Morphine by Intracerebroventricular Routes Produces Unexpected Antinociceptive Synergy in Rats

MATERIALS AND METHODS

Drugs

Oxycodone hydrochloride was a generous gift from The Boots Company (Australia) Pty Ltd (Sydney, Australia). Morphine hydrochloride was purchased from the Pharmacy Department, Royal Brisbane Hospital (Brisbane, Australia). All drugs were dissolved in isotonic saline for either i.c.v. or i.p. administration.

Animal

Male rats of both the Sprague-Dawley (200±40 g) and the Dark Agouti (180±30 g) strains were purchased from the Animal House, Faculty of Medicine, The University of Queensland and from The University of Queensland Central Breeding Facility, respectively. For the duration of the experiments, rats were housed in a room with a 12 h/12 h light dark cycle at a temperature of 21±2° C. and were given unlimited access to food and water.

Surgery

The technique for stereotaxic insertion of an indwelling stainless steel guide cannula into the left lateral ventricle of the rat brain has been described previously (Smith et al., 1990, Life Sci., 47, 579–585; Leow, K. P. and Smith, M. T., 1994, Life Sci., 54, 1229–1236). Sprague-Dawley rats were deeply anesthetized with a mixture of ketamine (100 mg kg$^{-1}$) and xylazine (16 mg kg)$^{-1}$ administered intraperitoneally. The skull was exposed and a hole drilled 1.5 mm L and 0.8 mm P with respect to bregma. The stainless steel guide cannula (21 G with a 45° bevel) was inserted stereotaxically to 1 mm above the left lateral ventricle (3.2 mm V) and fixed in position with dental cement. The wound was sutured and a stainless steel plug was inserted into the guide cannula. Rats received vancomycin (50,000 IU i.p.) to prevent infection and were kept warm during recovery from anaesthesia. Following cannula insertion, rats were housed singly for a recovery period of 5–7 days prior to i.c.v. drug administration.

Dosage Regimens

For i.c.v. experimentation, only Sprague-Dawley (SD) rats were used. After recovery from surgery, the rats were lightly anaesthetised with a mixture of $O_2/CO_2$ (50:50) and then either oxycodone, morphine or a combination of both opioids was administered via a single injection using a Hamilton 5 μL syringe. The $ED_{50}$ doses of oxycodone (78 nmol i.c.v.) and morphine (34 nmol i.c.v.) were reduced by approximately 50% to 40 nmol and 15 nmol respectively and administered to groups of SD rats in combination (n=12) and separately (n=4), by the i.c.v. route. This combination i.c.v. dose was further reduced to doses of 30 nmol oxycodone plus 10 nmol morphine (75% of the initial dose), and 20 nmol of oxycodone plus 7.5 nmol of morphine (50% of initial dose), and administered to additional groups of SD rats (n=4). Control rats (SD, n=4) received i.c.v. saline (1 μL)

Dark Agouti (DA) rats were chosen for the i.p. co-administration studies of oxycodone plus morphine, because they have been shown to have a limited ability to metabolise oxycodone to oxymorphone (the O-demethylated metabolite) compared with other rat strains (Cleary et al.,1994, J. Pharmacol. Exp. Ther. 271, 1528–1534). This step was taken to minimise the in vivo production of oxymorphone from oxycodone for two reasons, viz (i) oxymorphone has been reported to be present in very low concentrations (<1 ng/mL) in the plasma of humans dosed with oxycodone (Poyhia et al., 1992, Br. J. Clin. Pharmac. 33, 617–621; Ross et al., 1993, The Proceedings of the 7th World Congress on Pain, 533–534; Lacouture et al., 1996, The Proceedings of the 8th World Congress on Pain, 286), making DA rats a better model of human oxycodone metabolism than other rat strains, and (ii) as oxymorphone is a potent μ-opioid agonist with ten times the analgesic potency of morphine, its presence would potentially compromise our experiments.

DA rats were lightly anaesthetised with a 50:50 mixture of $O_2/CO_2$ and then administered either oxycodone or morphine or a combination of both drugs by a single i.p. injection, in groups of four for each dose. Rats were then placed in individual restraining cages and allowed to recover. Each rat received only one dose in any five day period to prevent potential acute opioid tolerance effects affecting the antinociceptive response. The minimum combined i.p. dose of oxycodone plus morphine producing a maximum antinociceptive response which persisted for the 3 h observation period, was determined experimentally. Initially, DA rats received oxycodone (2.85 μmol) plus morphine (3.11 μmol), because these doses were considerably lower than the previously published systemic $ED_{50}$ values for these opioids in DA rats (Cleary et al., 1994, supra). Thereafter, the doses of oxycodone and morphine were successively halved until the minimum combination i.p. dose that produced both maximum antinociception and an extended duration of action, was established.

Further groups of rats (n=4) were administered individual i.p. doses of morphine or oxycodone. Control rats received saline (0.5 mL i.p.).

Antinociceptive Assessment

The "Tail Flick Latency Test" (D'Amour, F. E. and Smith, D. L., 1941, J. Pharmacol. Exp. Ther., 72, 74–79) was used to quantify the degree of antinociception achieved in rats following i.c.v. and i.p. administration of oxycodone and morphine either individually or in combination. A cut-off time of 9 s was electronically maintained to minimise tissue damage to the rat's tail. Pre-injection reaction times were typically 3 to 4.5 s and were the average of two readings taken approximately 5 minutes apart. Tail flick latency times were measured following i.c.v. administration of oxycodone and morphine either individually or in combination at the following times 5, 10, 15, 30, 45, 60, 90, 120 and 180 minutes. After completion of an i.c.v. experiment, correct cannula placement was visually checked following an injection of malachite green dye (1 μL), decapitation and gross dissection of the brain.

Date Analysis

Tail flick latency times were converted to "The Percentage of Maximum Possible Effect" (%MPE) according to the following formula:

$$\% \ MPE = \frac{\text{(Postdrug latency)} - \text{(Predrug latency)}}{\text{(Maximum latency)} - \text{(Predrug latency)}} \times \frac{100}{1}$$

%MPE values >50% were regarded as indicating significant antinociception.

Statistical Analysis

Data were analyzed for significant differences using the paired Wilcoxon test or the unpaired Wilcoxon Rank-Sum test, where appropriate. The statistical significance criterion was $p<0.05$.

RESULTS

Figure 1B:
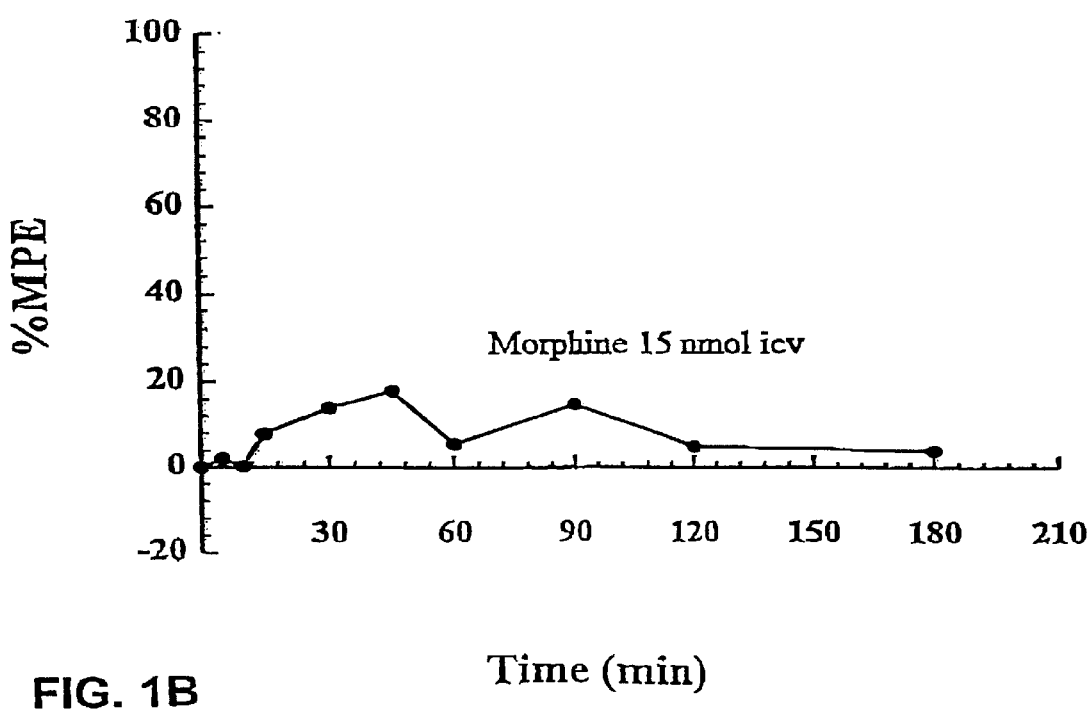

Following co-administration of oxycodone and morphine (40 nmol plus 15 nmol i.c.v. respectively) to SD rats, maximum antinociception (100% MPE) was achieved at 15 min post dosing and by 3 h post-dosing levels of antinociception were still greater than 50% MPE (FIG. 1). Reducing this dose to 30 nmol plus 10 nmol of oxycodone and morphine respectively, maximum antinociception was achieved but the duration of action was significantly shortened (90 min).

In comparison, when oxycodone (40 nmol i.c.v.) was administered alone, no antinociception was observed. In fact, most of the %MPE values were negative, indicating possible hyper-nociception at this dose (FIG. 1). Similarly when morphine (15 nmol i.c.v.) was administered alone, the levels of antinociception achieved were very low and the %MPE values did not exceed 20% at any time during the 3 h observation period (FIG. 1). The additive (summation of the independent antinociceptive effects) antinociceptive effects of i.c.v. oxycodone (40 nmol) plus morphine (15 nmol) were not significantly (p>0.05) different from baseline %MPE values obtained in rats dosed with saline (1 μL i.c.v.)

Figure 2A:
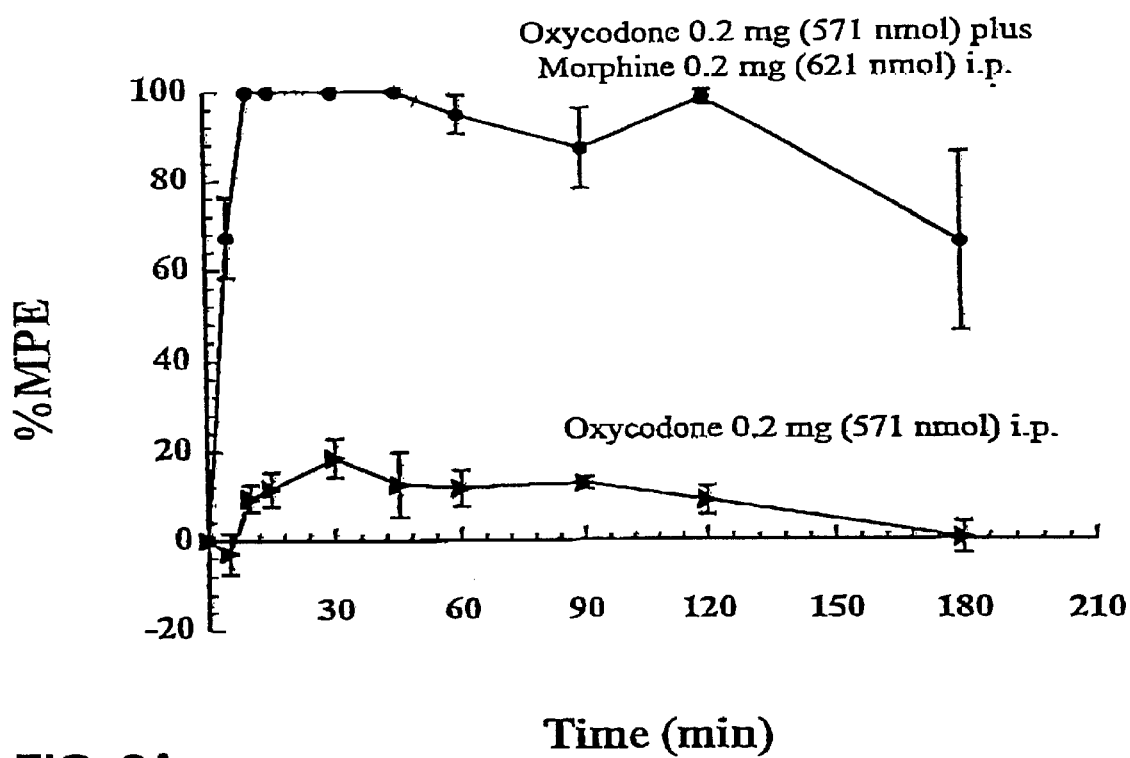
FIG. 2 shows the degree of antinociception (%MPE) as a function of time following i.p. administration to Dark Agouti rats of: 571 nmol oxycodone in combination with 621 nmol morphine; 571 nmol oxycodone solus; and 621 nmol morphine solus
Figure 2B:
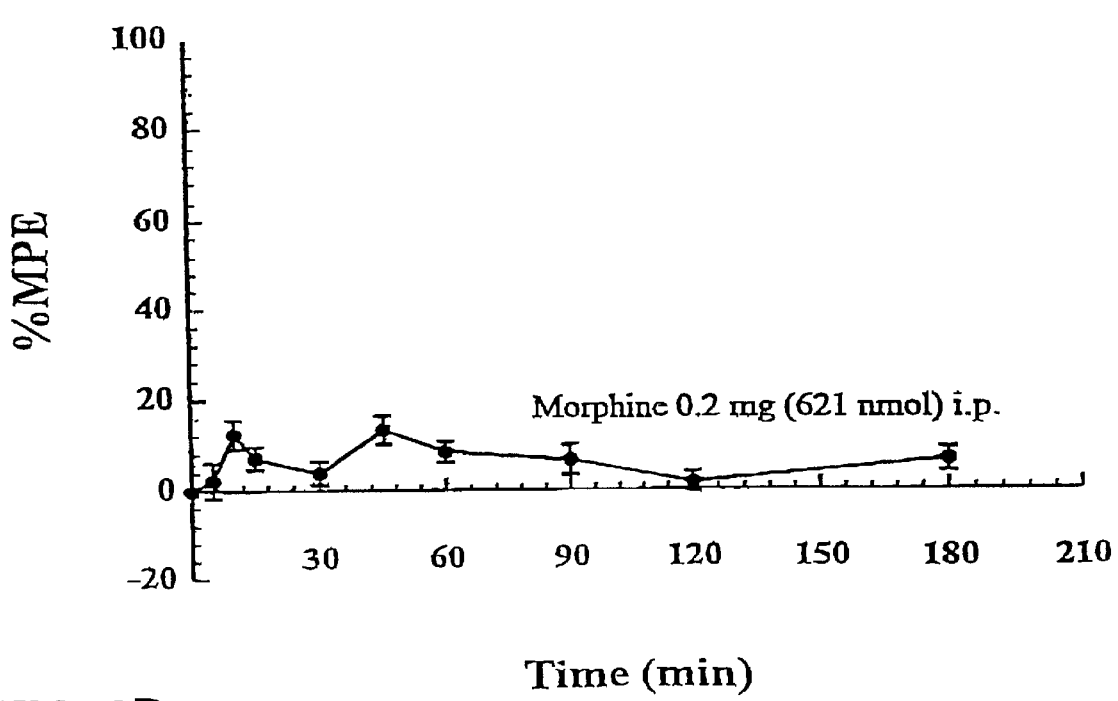

Following i.p. co-administration of morphine (3.11 μmol) plus oxycodone (2.85 μmol), 100% MPE values were achieved by 10 min post-dosing which did not decrease below this level for the duration of the experiment (180 min). Similarly, rats administered half this dose (1.42 nmol oxycodone plus 1.55 μmol morphine) also achieved maximum antinociception which persisted throughout the 180 min observation period. Further reducing the combined i.p. dose to 571 nmol of oxycodone plus 621 nmol of morphine, resulted in 100% MPE values by 10 min post-dosing with the mean %MPE value falling to approximately 65% by 180 min post-dosing (FIG. 2). However when the combination i.p. dose was reduced further still (285 nmol oxycodone plus 310 nmol morphine), 100% MPE was achieved only after 15–30 min postosing and the duration of action was significantly reduced to 90 min.

Rats that received individual doses of oxycodone (571 nmol) or morphine (621 nmol) did not achieve significant antinociception (>50% MPE) at any time post-dosing. When the antinociceptive effects of morphine (671 nmol) alone were summed with the antinociceptive effects of oxycodone (571 nmol) alone, the additive antinociceptive effects in DA rats were never greater than 50% MPE, during the 180 min observation period.

Following administration of the synergistic combination of morphine plus oxycodone, neither group of rats (Sprague-Dawley i.c.v., and Dark Agouti i.p.) displayed any adverse behavioural effects, such as sedation, incontinence and catatonia, one or more of which have been reported following large doses of either opioid alone. In fact, rats receiving the i.p. synergistic combination (571 nmol oxycodone plus 621 nmol morphine) were behaviourally similar to control rats that received saline.

DISCUSSION

The antinociceptive effects observed following individual intracerebroventricular (i.c.v.) administration of the opioid agonists, morphine and oxycodone, to Sprague-Dawley rats have been well characterized in our laboratory using the Tail Flick Latency Test. The $ED_{50}$ values for i.c.v. morphine and oxycodone have been determined to be 34 nmol and 78 nmol respectively (Leow, K. P. and Smith, M. T., 1994, supra). Our studies have now shown that co-administration of these two opioid agonists by the i.c.v. route in sub-antinociceptive doses (oxycodone 40 nmol plus morphine 15 nmol) results in unexpected antinociceptive synergy, characterised by an increase in the degree of antinociception from baseline values to 100% of the maximum possible effect. In addition, the duration of antinociception was also greatly increased, to over 180 min compared with 120 min and 90 min respectively for equipotent doses of morphine or oxycodone administered separately. A reduction in the combined dose of oxycodone plus morphine to 30 nmol and 10 nmol respectively, also produced maximum antinociception (100% MPE), but with the duration of action shortened to 90 min.

Furthermore, antinociceptive synergy was also observed following co-administration of subanalgesic doses of both drugs (oxycodone 571 nmol plus morphine 621 nmol) by the intraperitoneal route to male Dark Agouti rats, which metabolize oxycodone to oxymorphone (a potent $\mu$-opioid receptor agonist) to a lesser extent than do other strains of rats. This synergy was characterized by a rapid onset of maximum antinociception (<10 min) with an extended duration of action (>180 min) compared with either drug administered individually. Compared with rats that received individual i.c.v. or i.p. doses of morphine or oxycodone, the magnitude of the synergistic analgesic effects was in a range of 5–20 fold.

Rats dosed with the synergistic combination of the two strong opioids, oxycodone and morphine, by both i.p. and i.c.v. routes displayed no observable adverse behavioral effects, such as catatonia, respiratory depression or marked sedation. Extrapolation of these findings in rats to humans, suggests that co-administration of sub-analgesic doses of two strong opioids such as morphine and oxycodone, contrary to the World Health Organization's (WHO) guidelines for cancer pain relief (1986), will provide excellent analgesia, whilst minimizing unacceptable side-effects.

EXAMPLE 2

The Intrinsic Antinociceptive Effects of Oxycodone Appear to Be Kappa-opioid Receptor Mediated Oxycodone is a semi-synthetic opioid analgesic derived from the naturally occurring alkaloid, thebaine. In humans, oxycodone has been shown to have an analgesic potency 0.7 times that of morphine after systemic administration (Beaver et al., 1978, J. Pharmacol. Exp. Ther, 207, 92–100; Kalso et al., 1990, Pharmacol. Toxicol., 67, 322–328). Although oxycodone has been used clinically for over 75 years, little is known about the intrinsic pharmacology of this drug. Variously, oxycodone has been thought to induce analgesia by a similar mechanism to morphine or it has been proposed to be a prodrug for an analgesically active metabolite such as oxymorphone (Beaver et al., 1978, supra), its O-demethylated derivative. Oxymorphone is a potent $\mu$-opioid receptor agonist with 10 times the potency of morphine (Beaver et al., 1977, J. Clin. Pharmacol., 17, 186–198). Recently, however, the putative role of oxymorphone as an analgesically active metabolite of oxycodone has been questioned. In human plasma and urine, levels of unconjugated oxymorphone have been reported to be undetectable (<1 $ngml^{-1}$) after administration of oxycodone (Poyhia et al., 1992, supra). In addition, Dark Agouti rats that are deficient in the enzymes required to O-demethylate benzomorphan opioids, achieved maximum antinociception following subcutaneous administration of oxycodone (Cleary et al., 1994, supra). Furthermore, when oxycodone was administered by the i.c.v. route to rats, preventing any form of hepatic metabolism, maximum antinociception was observed within 7 min of dosing ($ED_{50}$=78 nmol, c.f $ED_{50}$= 34 nmol for morphine), indicating that oxycodone itself has intrinsic antinociceptive properties (Leow K. P. and Smith M. T., 1994, supra). This antinociception was completely reversible by naloxone (55 nmol icv), indicating that the antinociceptive effects of oxycodone are mediated by opioid receptors (Leow K. P. and Smith M. T., 1994, supra).

Given that naloxone is a universal opioid receptor antagonist that does not effectively discriminate between the three major classes of opioid receptors, $\mu$, $\delta$ and $\kappa$, it is not possible to determine the specific class of opioid receptor mediating the antinociceptive effects of oxycodone unless more selective antagonists are utilized. Naloxonazine (nalz) has been reported to be an irreversible $\mu_1$-selective opioid receptor antagonist provided it is administered 24 h prior to administration of the corresponding opioid receptor agonist. Nalz has been shown to antagonise the antinociceptive effects of both morphine and the $\mu$-selective opioid peptide enkephalin-[D-Ala$^2$,N-Phe$^4$,Gly-ol$^5$] (DAMGO) (Pastemak, G. and Wood, P., 1986, Life Sci., 38, 1889–1898). In contrast nalz did not reduce the antinociception observed following administration of the $\delta$-selective opioid peptide agonist, enkephalin-[D-Pen$^{2,5}$] (DPDPE) (Nishimura et al., 1984, Mol. Pharmacol., 25, 29–37; Hahn et al., 1982, J. Neurosci., 2, 572–576; Johnson, N. and Pasternak, G. W., 1984, Mol. Pharmacol., 26, 477–483). Naltrindole (NTI) has been reported to be a non-peptide $\delta$-opioid receptor antagonist with a 100-fold selectivity for $\delta$-opioid receptors relative to $\mu$-opioid receptors, and a 10,000-fold selectivity for $\delta$-relative to $\kappa$-opioid receptors (Portoghese et al., 1988a, J. Med. Chem., 31, 281–282; Portoghese et al., 1988b, Eur. J. Pharmacol., 146, 185–186). Similarly, nor-binaltorphimine (nor-BNI) has been reported to be an irreversible $\kappa$-opioid receptor antagonist that will antagonize the antinociceptive effects of both benzacetamide (U69,593) and benzomorphan (bremazocine) $\kappa$-opioid receptor agonists (Takemor et al., 1988, supra; Horan et al., 1991, J. Pharmacol. Exp. Ther., 257, 1154–1161).

Therefore the aim of this set of experiments was to determine the major class of opioid receptors mediating the antinociceptive effects of oxycodone following i.c.v. administration to rats, by i.c.v. administration of selective opioid receptor antagonists.

MATERIALS AND METHODS

Drugs

Oxycodone hydrochloride was a generous gift from The Boots Company (Australia) Pty Ltd (Sydney, Australia). Morphine hydrochloride was purchased from the Pharmacy Department, Royal Brisbane Hospital (Brisbane, Australia). Naloxonazine, naltrindole, nor-binaltorphimine, (5α,7α,8β)-(+)-N-methyl-N-[7-(1-pyrrolidinyl)-1-oxaspiro[4.5]dec-8-yl]-benzeneacetamide (U69,593), trans-(+)-3,4-dichloro-N-methyl-N-[2-(1-pyrrolidinyl)-cylcohexyl]-benzeneacetamide methanesulfonate (U50,488H), bremazocine and DPDPE were purchased from Research Biochemicals Inc (Sydney, Australia). Xylazine and ketamine were purchased from Bayer (Sydney, Australia) and Marlab (Brisbane, Australia) respectively.

Animals

Ethical approval for this set of experiments was obtained from the Animal Experimentation Ethics Committee of The University of Queensland. Male Sprague-Dawley rats (200±40 g) were purchased from the Faculty of Medicine Animal Breeding Facility, The University of Queensland. Rats were housed in a temperature controlled environment (20±2° C.) with a 12 h/12 h light/dark cycle and free access to both food and water.

Surgery

Surgery was performed as described in Example 1.

Dosage Regimens

I.c.v. injections were made using a 5 μL Hamilton syringe with a 25 gauge needle under light anaesthesia (50% $O_2$/50%$CO_2$) and all drugs were dissolved in isotonic saline. All rats were tested for correct cannula placement 5–7 days after surgery by injecting a single dose of oxycodone (200 nmol icv) and measuring the tail flick latency for the first 10 min post-injection. Rats that displayed no antinocicepbon were omitted from the study as previous experience had shown that a lack of antinociception was due to incorrect cannula placement. Groups of rats for each selective opioid antagonist included in the study were give a further 2–3 days recovery period. These received i.c.v. administration of the appropriate selective opioid antagonist followed by oxycodone (200 nmol).

Additional groups of rats received the selective opioid antagonist followed by the corresponding selective opioid agonist (positive controls) or saline (1 μL i.c.v.) (n=4). Nalz (1.0 nmol) (n=4) and nor-BNI (0.3 nmol) (n=8) were injected 24 h prior to i.c.v. administration of the opioid agonists to ensure that only the irreversible opioid antagonist effects were being studied (Clark et al., 1988, Mol. Pharmacol., 34, 308–317). In contrast the competitive δ-opioid antagonist naltrindole (1 nmol, i.c.v.) (n=4), was administered only 15 min prior to i.c.v. administration of opioid agonists or saline.

Antinociceptive Assessment

The Tail Flick Latency Test (D'Amour, F. E. and Smith, D. L., 1941, supra) described in Example 1 was used to quantify the degree of antinociception achieved in rats following i.c.v administration of opioid agonists or saline.

Data Analysis

Tail Flick Latency times were converted to The Percentage of Maximum Possible Effect (%MPE) according to the formula described in Example 1.

Statistical Analysis

Data were analysed for significant differences as described in Example 1.

RESULTS

Figure 3A:
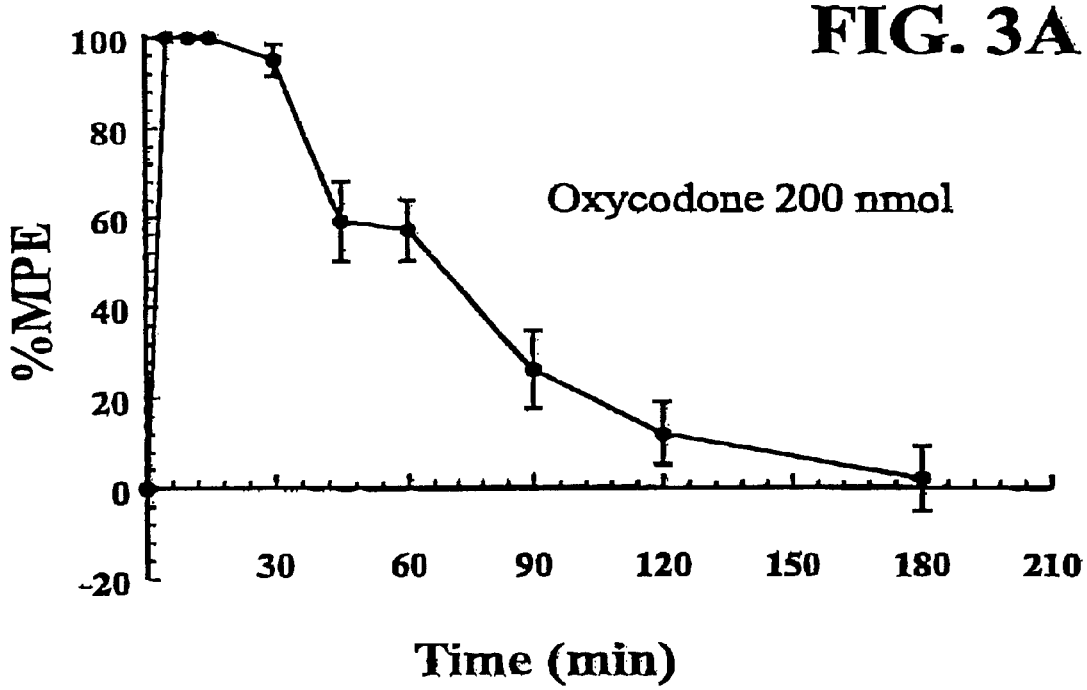
FIG. 3 shows the degree of antinociception observed following i.c.v. administration of (A) oxycodone (200 nmol), (B) morphine (78 nmol).

The antinociception observed following i.c.v. oxycodone (200 nmol) administration reached peak values of 100% MPE at 5 min post-dosing, thereafter decreasing in a monoexponential manner reaching baseline values by 90 min post-dosing (FIG. 3A). In contrast, the antinociceptive effects observed in control rats that received i.c.v. saline (1 μL) were not significantly different from baseline values (p>0.05) throughout the 3 h study period (data not shown).

Figure 3B:
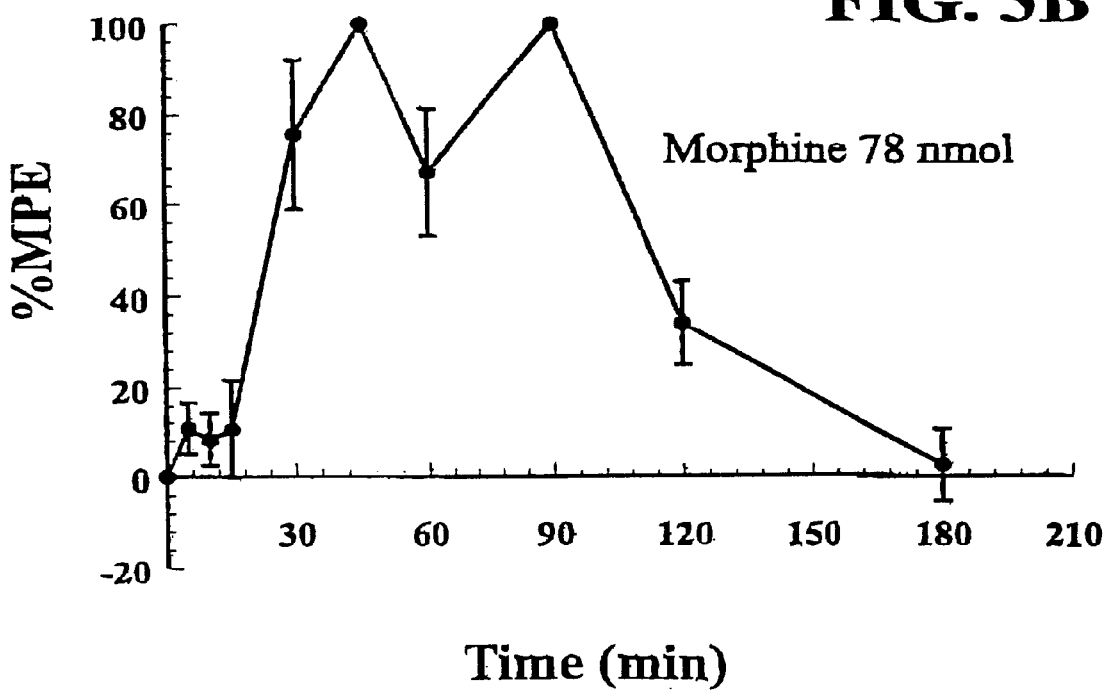
Figure 4A:
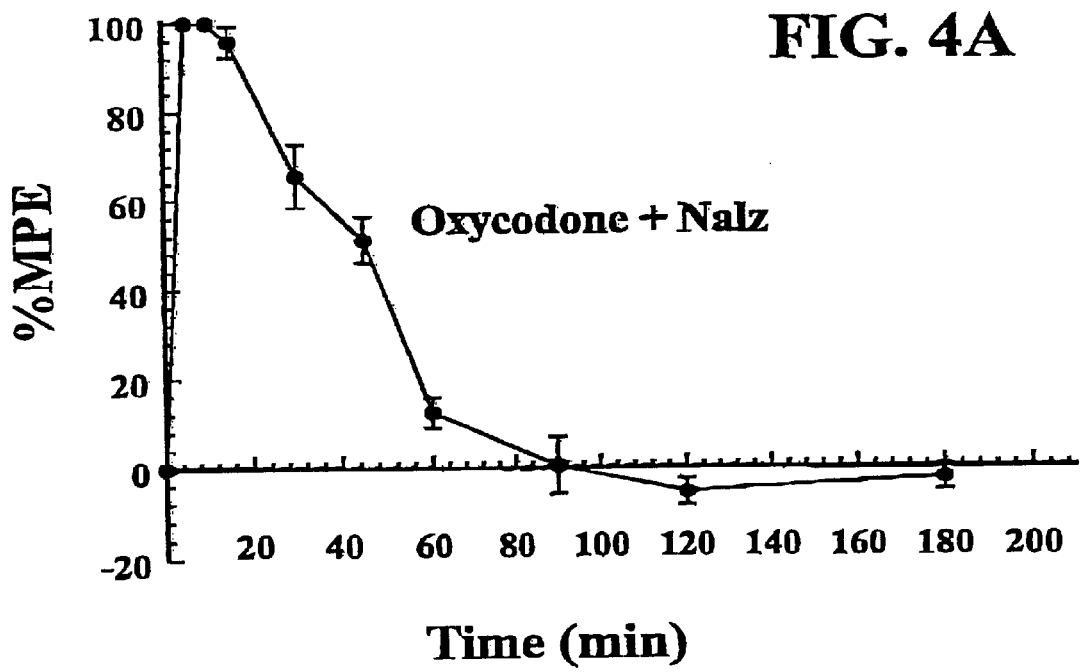
FIG. 4 shows the degree of antinociception observed following i.c.v. administration of the $\mu_1$-selective opioid receptor antagonist naloxonazine (1 nmol) 24 h prior to i.c.v. administration of (A) oxycodone (200 nmol) and (B) morphine (78 nmol).
Figure 4B:
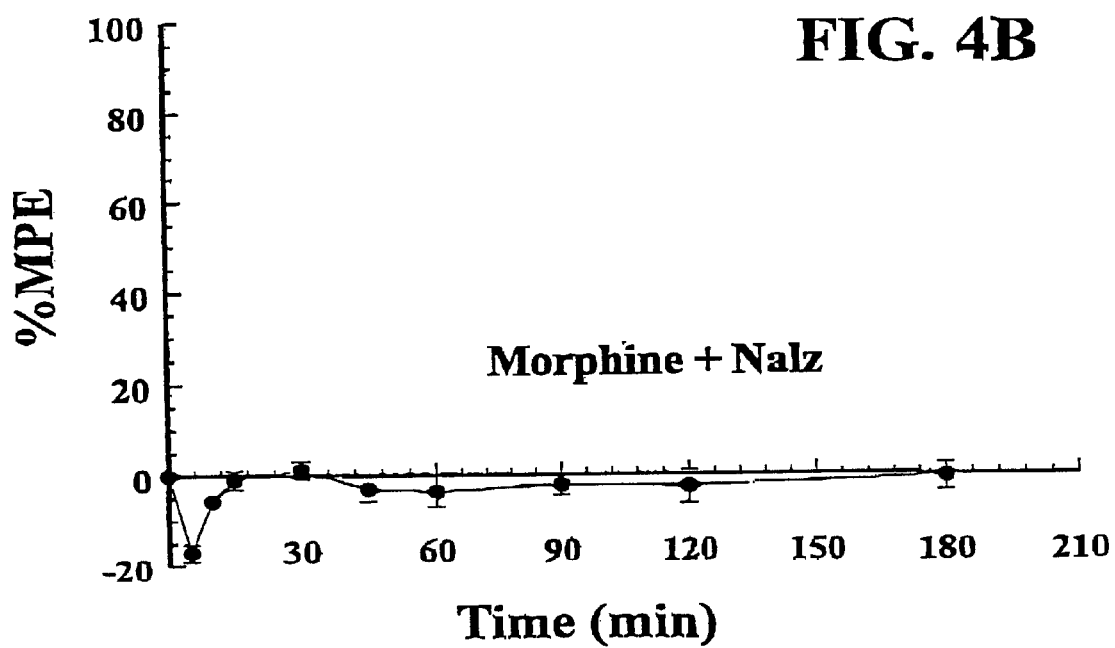

Administration of the irreversible $\mu_1$-opioid receptor antagonist, naloxonazine (1 nmol i.c.v.) 24 h prior to administration of oxycodone (200 nmol i.c.v.) had a minor effect on the observed antinocicepfion. The duration of action of oxycodone was shortened from 90 min to 60 min but the magnitude of antinociception did not appear to be significantly reduced during the first 15 min (FIG. 4A), when compared with rats receiving oxycodone (200 nmol i.c.v.) alone (FIG. 3A). However, naloxonazine completely attenuated the antinociceptive effects of morphine (78 nmol, i.c.v.) administered to the same rats 24 h later (FIG. 4B). In contrast, this same dose of morphine administered alone to rats by the i.c.v. route produced maximum antinociception which decreased in a biphasic manner over the 3 h study period (FIG. 3B).

It was also noted that the %MPE values observed in control rats that received nalz (1 nmol i.c.v.) followed 24 h later by saline (1 μL) were 5–10% lower than those of untreated rats indicating that nalz may have been interfering with the normal functioning of the endogenous opioidergic receptor system. Rats treated with nalz displayed minor excitatory behaviour (shaking and teeth chattering) immediately after dosing, and 24 h later they appeared to be more sensitive to external stimuli (touch and sound) than untreated rats.

Figure 5A:
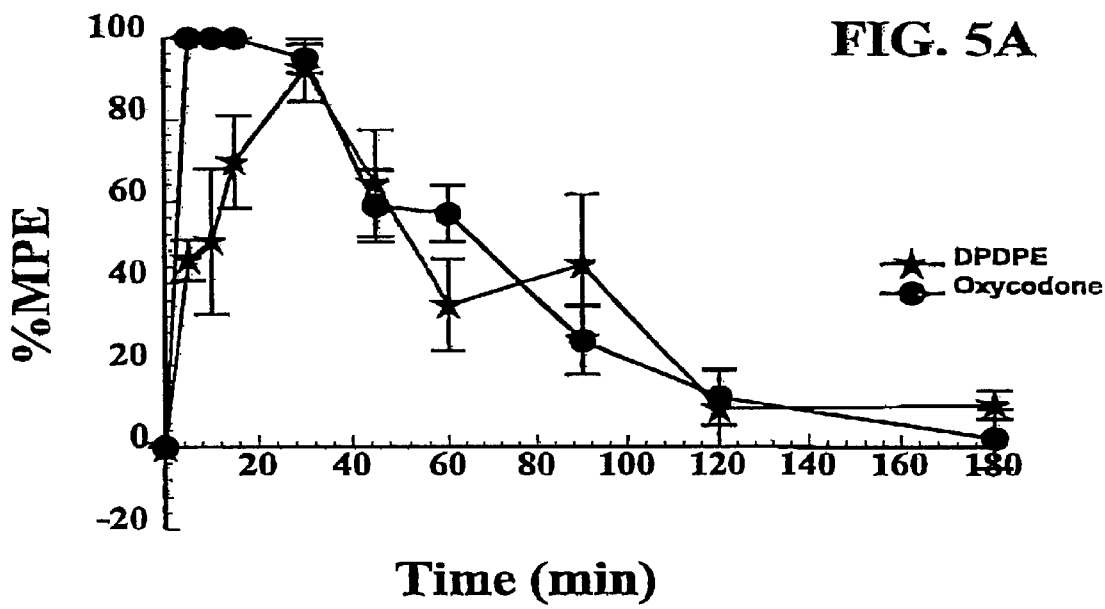
FIG. 5 shows the degree solus of antinociception observed following: (A) i.c.v administration of oxycodone and the δ-selective opioid against DPDPE solus; and (B) i.c.v. administration of the δ-selective opioid antagonist, naltrindole (1 nmol) administered 15 min prior to oxycodone (200 nmol) and 15 min prior to DPDPE (45 nmol)
Figure 5B:
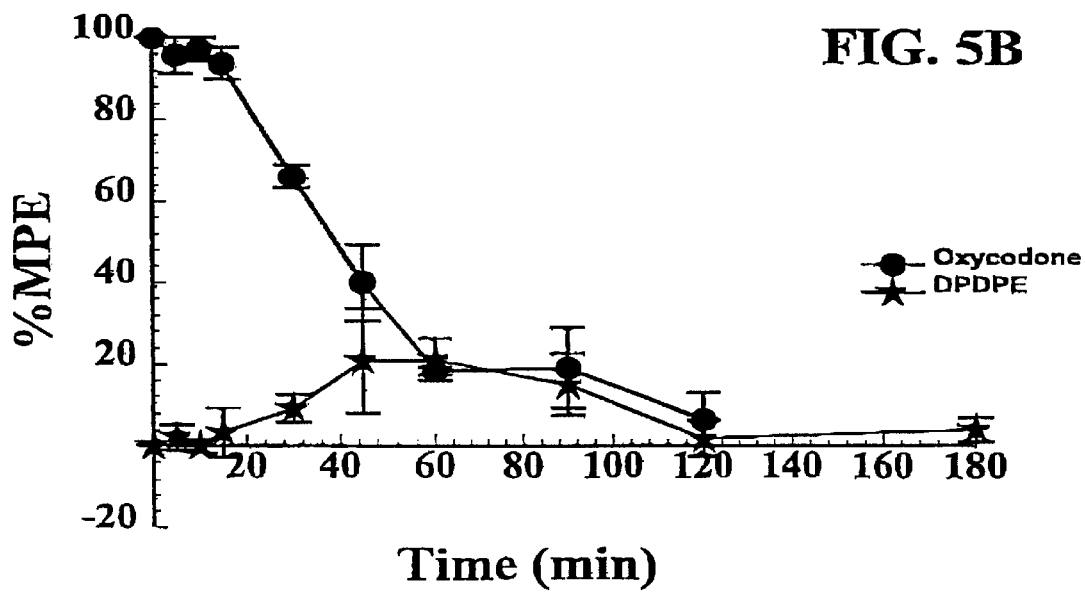
Figure 6A:
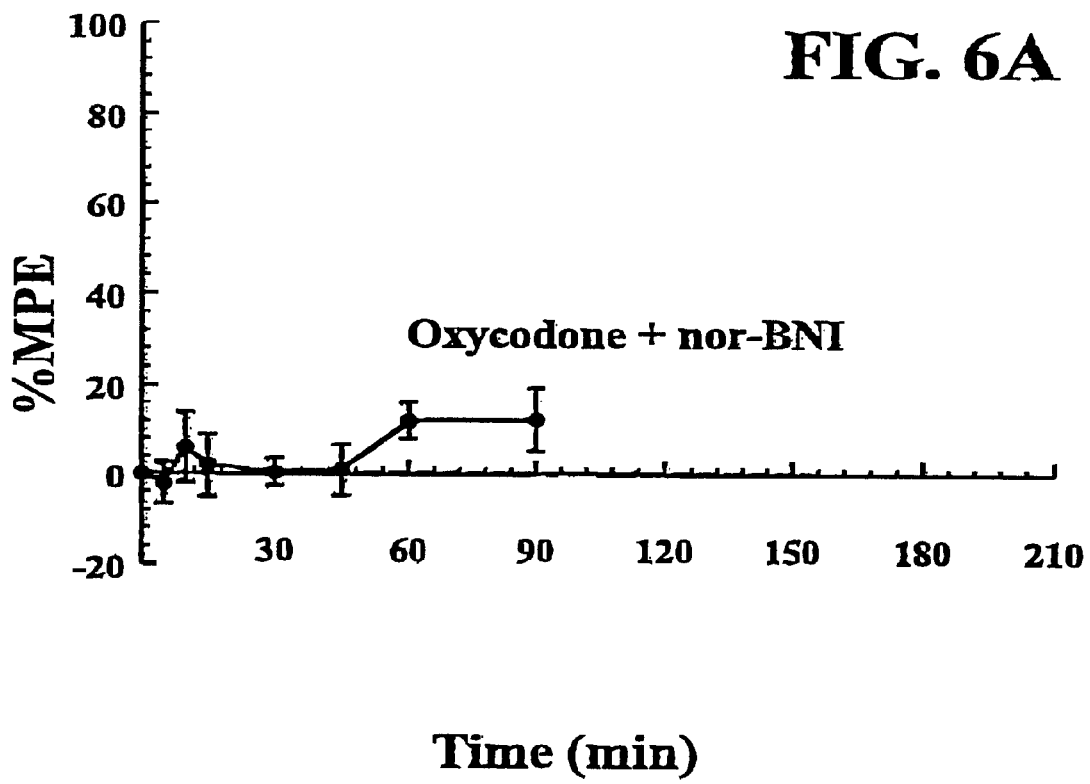
FIG. 6 shows the degree of antinociception observed following nor-BNI (0.3 nmol) administration 24 h prior to i.c.v. administration of (A) oxycodone (200 nmol), (B) U69,593 (133 nmol), (control data for U69,593 (133 nmol i.c.v.) in untreated rats is also shown), (C) bremazocine (57 nmol) and (D) morphine (78 nmol)
Figure 6B:
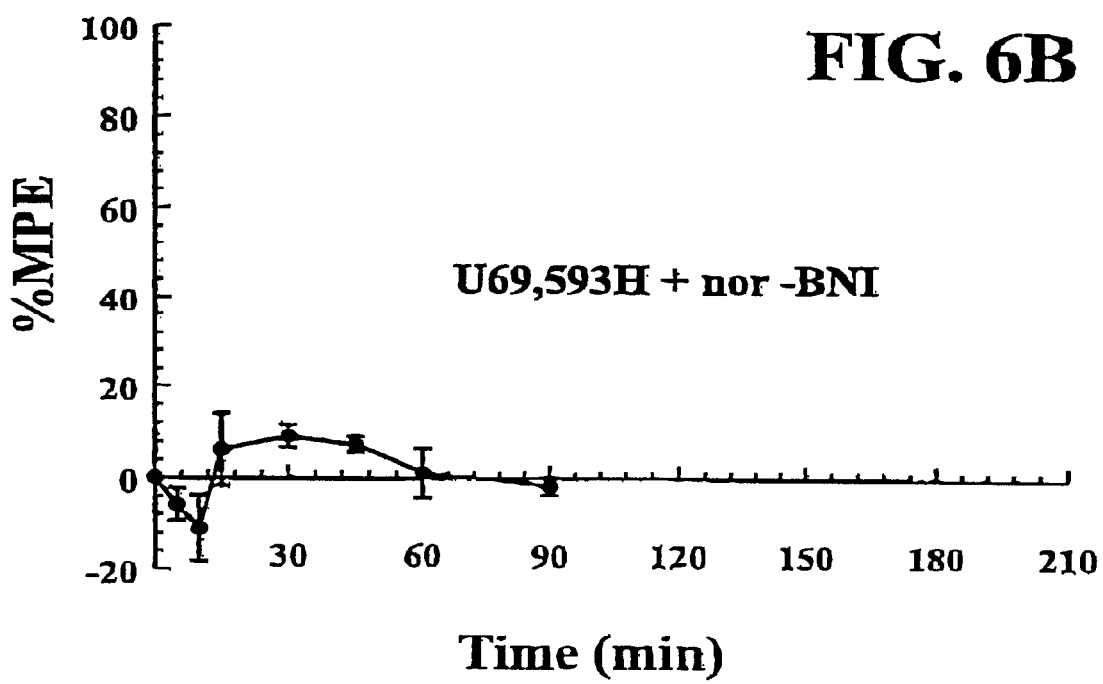
Figure 6C:
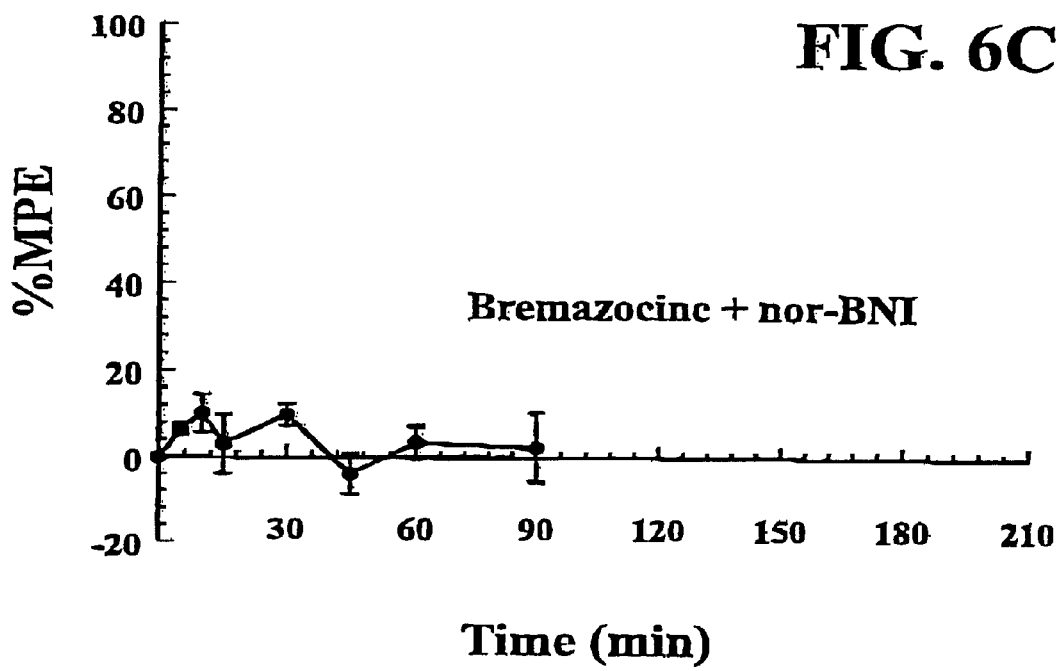
Figure 6D:
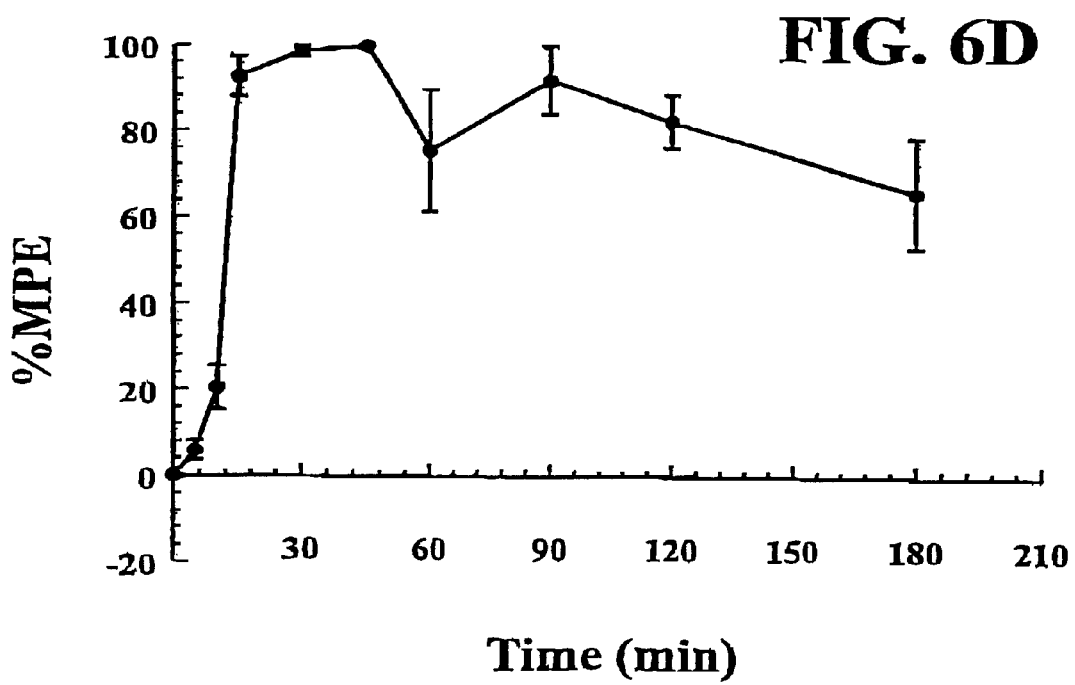

Administration of the competitive δ-opioid receptor antagonist, naltrindole (2.2 nmol i.c.v.), 15 minutes prior to oxycodone (200 nmol i.c.v.) administration, did not significantly attenuate (p>0.05) the antinociceptive effects of oxycodone (FIG. 5B) when compared to the control experiment (FIG. 5A). However, naltrindole significantly attenuated (p<0.05) the antinociceptive effects of the selective δ-opioid receptor agonist DPDPE (45 nmol) (FIG. 5B) in comparison with the control experiment (FIG. 5A). Rats that received naltrindole (1 nmol i.c.v.) followed 15 min later by saline (1 μL) exhibited %MPE values that were no not significantly different (p>0.05) from pre-dosing baseline values In contrast, i.c.v. administration of the κ-selective opioid receptor antagonist nor-BNI (0.3 nmol), 24 h prior to the i.c.v. administration of oxycodone (200 nmol), U69,593 (133 nmol) or bremazocine (57 nmol), resulted in complete attenuation of the antinociceptive effects of each of these compounds (FIGS. 6A–C respectively). Importantly, however, the antinociceptive effects of morphine (78 nmol i.c.v.) were not attenuated (FIG. 6D).

Behaviorally, rats that received oxycodone (200 nmol i.c.v.) did not exhibit any signs of spontaneous bladder emptying or incontinence in contrast to rats that received i.c.v. morphine (78 nmol), nor did they exhibit the catatonic behaviour observed in rats which had received oxycodone systemically (Poyhia, R. and Kalso, E., 1992, 70, 125–130; Cleary et al., 1994, supra).

DISCUSSION

Our previous studies (Leow, K. P. and Smith, M. T., 1994, supra) have shown that administration of oxycodone or morphine by the i.c.v. route produces naloxone-reversible antinociceptlon. However, the degree of antinociception versus time profiles for the two opioid drugs are very different (Leow K. P. and Smith, M. T., 1994, supra). Oxycodone has a much faster onset of maximum antinociception (5–7 min) compared with the 30–45 min required for morphine. The antinociceptive effects of i.c.v. morphine are biphasic in nature with the initial phase being due to activation of supraspinal $\mu$-opioid receptors and the second phase (onset=90 min post dosing) probably resulting from caudal redistribution of morphine, activating spinal $\mu$-opioid receptors (Leow, K. P. and Smith, M. T., 1994, supra).

In contrast, oxycodone shows only a single phase of antinociception after i.c.v. administration which is essentially complete by 90 min post-dosing (Leow, K. P. and Smith, M. T., 1994, supra). This is not surprising as the potency of oxycodone administered by the intrathecal (i.t.) route has been reported to be only 0.09 times that of i.t. morphine (Yaksh. T. L. and Hartey, G. J., 1987, J. Pharmacol. Exp. Ther., 244, 501–507; Poyhia, R. and Kalso, E., 1991, supra), indicating that oxycodone has poor affinity for spinal opioid receptors. Thus, redistribution of oxycodone from supraspinal sites at the time of the i.c.v. injection to the spinal region by 90 min post-injection would result in a reduction of antinociception to baseline values at this time. Furthermore, studies using [$^3$H]-DAMGO have shown that the affinity of oxycodone for the $\mu$-opioid receptor is low compared with that of morphine (Chen et al., 1991, Life Sci., 48, 2165–2171). Thus for all of the above reasons, it is unlikely that oxycodone elicits its antinociceptive actions through the same class of opioid receptors as morphine.

This notion is further supported by (i) the report of Pasternak and Wood (1986) that $\mu_1$-opioid receptors mediate the antinociception observed following i.c.v. morphine administration and (ii) our observation that the $\mu_1$-selective opioid receptor antagonist, naloxonazine, attenuated the antinociceptive effects of i.c.v. morphine but had almost no effect on the antinociception observed following i.c.v. oxycodone administration. In addition, our studies have shown that i.c.v. administration of the $\delta$-selective opioid receptor antagonist, naltrindole, also failed to attenuate the antinociceptive effects of icv oxycodone. Taken together, these results indicate that the intrinsic antinociceptive effects of oxycodone are not mediated by either $\mu_1$ or $\delta$-opioid receptors.

In contrast, when the irreversible $\kappa$-selective opioid antagonist, nor-BNI was administered by the i.c.v. route in a dose of 0.3 nmol, 24 hours prior to icv administration of oxycodone or the $\kappa$-opioid agonists U69,593 (133 nmol i.c.v.) and bremazocine (57 nmol i.c.v.), the antinociceptive effects of all three compounds were markedly attenuated. However, i.c.v, administration of nor-BNI (0.3 nmol i.c.v.) 24 h pror to morphine (78 nmol i.c.v.) had no effect on morphine's antinociceptive response (FIG. 6D). These results strongly suggest the involvement of $\kappa$-opioid receptors in the intrinsic antinociceptive effects of oxycodone. This conclusion is further supported by the observation that i.c.v. administration of known $\kappa$-opioid agonists of both the benzacetamide (U50,488H and U69,593, Leighton et al., 1988, Br. J. Pharmacol., 93, 553–560) and the benzomorphan classes (bremazocine and ethylketazocine, Horan et al., 1991, supra) induce antinociception characterised by a rapid onset of action and a single antinociceptive phase in a manner analogous to that observed following icv oxycodone dosing.

In summary, the studies described in Example 2 strongly suggest that the intrinsic antinociceptive effects of oxycodone are mediated by $\kappa$-opioid receptors, in contrast to morphine which interacts primarily with $\mu$-opioid receptors. However, given that at least three $\kappa$-opioid receptor subtypes have been pharmacologically defined (Von Voightlander et al., 1983, J. Pharmecol. Exp. Ther., 224, 525–530; Nock et al., 1988, Life Sci., 42, 2403–2412; Clark et al., 1989, J. Pharmacol. Exp. Ther., 251, 461–468), further studies were required to determine which of these subtypes mediate the antinociceptive effects of oxycodone which are described hereinafter.

EXAMPLE 3

Following intracerebroventricular (i.c.v) administration of oxycodone to adult male Sprague-Dawley (SD) rats, oxycodone elicits naloxone-reversible (i.e., opioid receptor-mediated), intrinsic pain-relieving (antinociceptive) effects with a potency equal to approximately half (44%) that of morphine administered by the same route (Leow, K. P. and Smith, M. T., 1994, supra). The studies described in Example 2, involving the i.c.v. administration of selective $\mu$-, $\delta$- and $\kappa$-opioid receptor antagonists, have shown that the intrinsic antinociceptive effects of oxycodone are completely attenuated by i.c.v. administration of the selective $\kappa$-opioid receptor antagonist, nor-binaltorphimine (nor-BNI), in doses that did not attenuate the antinociceptive effects of i.c.v. morphine ($\mu$-opioid agonist). Additionally, the $\mu_1$-opioid receptor antagonist, naloxonazine and the $\delta$-opioid receptor antagonist, naltrindole, did not attenuate the antinociceptive effects of i.c.v. oxycodone in doses that completely attenuated the antinociceptive effects of i.c.v. morphine ($\mu$-opioid agonist) and i.c.v. DPDPE ($\delta$-opioid agonist) respectively (Ross, F. B. and Smith, M. T., 1997, in press). Taken together these results indicate that oxycodone elicits its intrinsic pain-relieving effects through $\kappa$-opioid receptors. Although there are 3 major subtypes of $\kappa$-opioid receptors in the CNS, viz. $\kappa_1$, $\kappa_2$ and $\kappa_3$, (Clark et al. 1989, supra; Lai et al. 1994, Neuroreport, 5, 2161–2164; Ni et al. 1995, Peptides, 16, 1083–1095), nor-BNI reportedly binds with high affinity to only $\kappa_1$- and $\kappa_2$-opioid receptors (Takemori et al., 1988, supra; Ni et al., 1993, Peptides, 14, 1279–1293), suggesting that oxycodone elicits its intrinsic pain-relieving properties through $\kappa_1$- and/or $\kappa_2$-opioid receptors. Therefore this set of experiments was designed to further investigate the class(es) and subtypes of opioid receptors mediating oxycodone's intrinsic antinociceptive effects by using in vitro brain homogenate binding techniques. Specifically this study was designed (i) to characterize the opioid receptor binding profiles of oxycodone against the selective $\mu$-, $\delta$- and $\kappa_1$-radioligands ([$^3$H] morphine, [$^3$H]DPDPE, [$^3$H]U69,593 respectively) relative to the binding profiles of the respective unlabelled ligands, morphine, DPDPE, bremazocine, and (ii) to compare the binding profiles of oxycodone with the results of our studies described in Example 2.

MATERIALS AND METHODS

Materials

[$^3$H]Morphine (84.5 Ci/mmol), [$^3$H]U69,593 (47.4 Ci/mmol) and [$^3$H]DPDPE-Cl ([2,5-D-Penicillamine, 4-p-Cl-phenylalanine]enkephalin) (48.6 Ci/mmol) were purchased from New England Nuclear Corporation (Boston, USA). Naloxone hydrochloride, DPDPE, 2-hydroxyethylpiperazine-N-2-ethane sulphonic acid (HEPES), Tris.HCl and bremazocine hydrochloride were purchased from Sigma-Aldrich (Sydney, Australia). Oxycodone hydrochloride was a generous gift from Boots Australia Pty Ltd (Sydney, Australia). Morphine hydrochloride was purchased from the Royal Brisbane Hospital Pharmacy Adult male Sprague-Dawley rats (200 g) were purchased from the Faculty of Medicine Animal House, The University of Queensland. Adult male albino guinea-pigs were obtained from the Central Animal Breeding Facility of The University of Queensland. Ethical approval for these experiments was obtained from the Animal Experimentation Ethics Committee of The University of Queensland.

Methods

Brain Membrane Preparation

Following decapitation, rat or guinea-pig brains were removed and placed in ice-cold sucrose solution (0.32 M), frozen at −20° C. for 24 h and then at −80° C. until use. After thawing, brain tissue was homogenized for 1 min in ice-cold (4° C.) HEPES-tris buffer (50 mM, pH 7.4) in a volume of 10 mL/g wet weight of tissue. Tissue homogenate was then centrifuged (40,000 g for 45 min), the supernatant decanted and the membranes resuspended in HEPES-tris buffer prior to a 45 min incubation at 37° C. to remove endogenous opioid peptides. Membranes were then centrifuged twice and resuspended in 10 mL of buffer per g wet weight of original tissue and stored at −80° C. until required. Protein concentrations were determined by the method of Lowry et el (1951).

Radioligand Binding Assays

Ligand binding assays for each of the major classes of opioid receptors ($\mu$-, $\delta$- and $\kappa_1$) were performed using rat brain homogenate preparation and guinea-pig brain homogenate in the case of $\kappa_1$-opioid receptor binding. Aliquots (0.1 mL) of resuspended membrane preparation were added to tubes containing 0.05 mL of the radioligand of interest, 0.05 mL of unlabelled ligand of interest, and 0.3 mL of HEPES-tris buffer (50 mM, pH 7.4). Samples were incubated in triplicate for 1 h with one of the following radioligands: [$^3$H]morphine, [$^3$H]DPDPE-Cl or [$^3$H]U69,593 and a range of concentrations (100 pM–100 $\mu$M) of the appropriate unlabelled ligand (morphine, DPDPE, bremazocine, oxycodone). Sample incubations were stopped by filtration using Whatman GF/B glass fibre filters presoaked in 1% polyethylenelmine, using a Brandell Cell Harvester, and washed three times with 1 mL aliquots of icecold HEPES-tris buffer (50 mM, pH 7.4). Binding assays were performed at room temperature (25° C.) except when [$^3$H]U69,593 was used as the radioligand when the incubation temperature was 37° C. The filter papers with retained radioligand were placed in scintillation fluid (4 mL) in scintillation vials for 12 h prior to liquid scintillation spectrophotometry using a Packard scintillation counter (Tricarb 2700 TR) with quenching correction facilities. These experiments were repeated using three different rat and/or guinea-pig brain tissue homogenate preparations.

RESULTS

Figure 7:
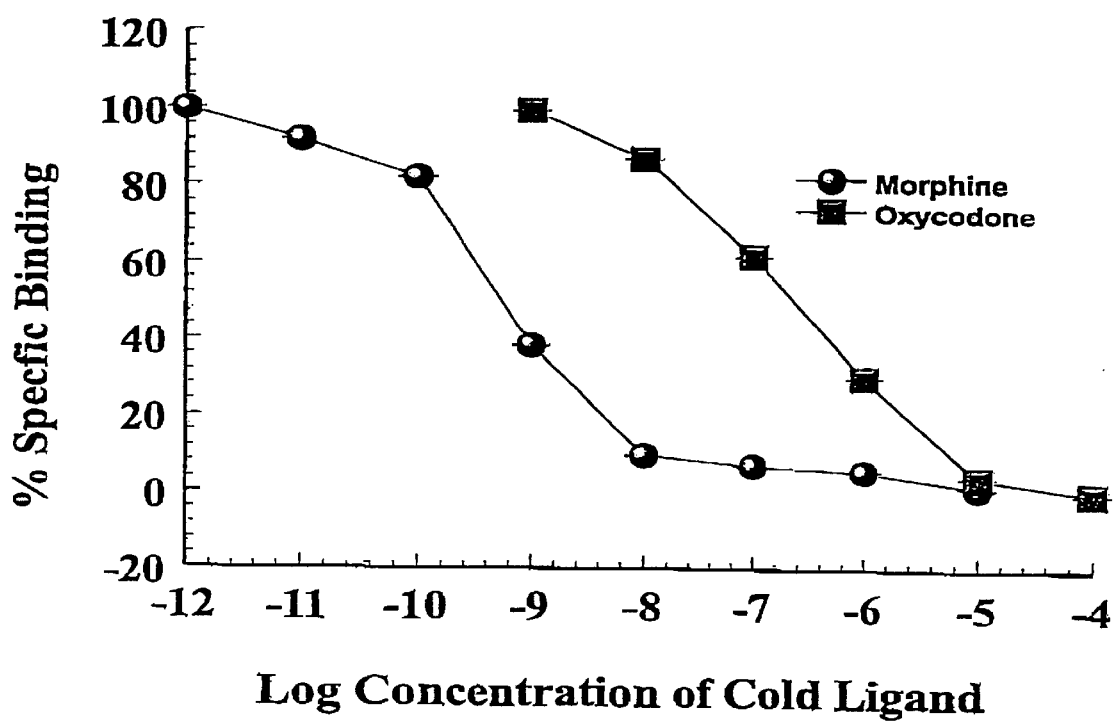
FIG. 7 refers to representative displacement curves of oxycodone and morphine against $^3$H-morphine in rat brain membranes.

The binding affinity of oxycodone for each of the major classes of opioid receptors ($\mu$-, $\delta$- and $\kappa_1$) was determined using selective opioid receptor binding assays in brain tissue homogenate preparations as described above. Oxycodone displaced [$^3$H]morphine ($\mu$-opioid receptor agonist) with low affinity ($K_i$=349 nM, FIG. 7) whereas unlabelled morphine itself displaced [3H]morphine with a high affinity ($K_D$=1.1 nM) similar to values reported in the literature (Raynor et al. 1994, J. Pharmacol. Exp. Ther., 45, 330–334). However the Hill coefficient for the inhibition binding curve of oxycodone against [$^3$H]morphine was low (0.72), indicating that oxycodone does not bind to the high affinity morphine binding site.

Figure 8:
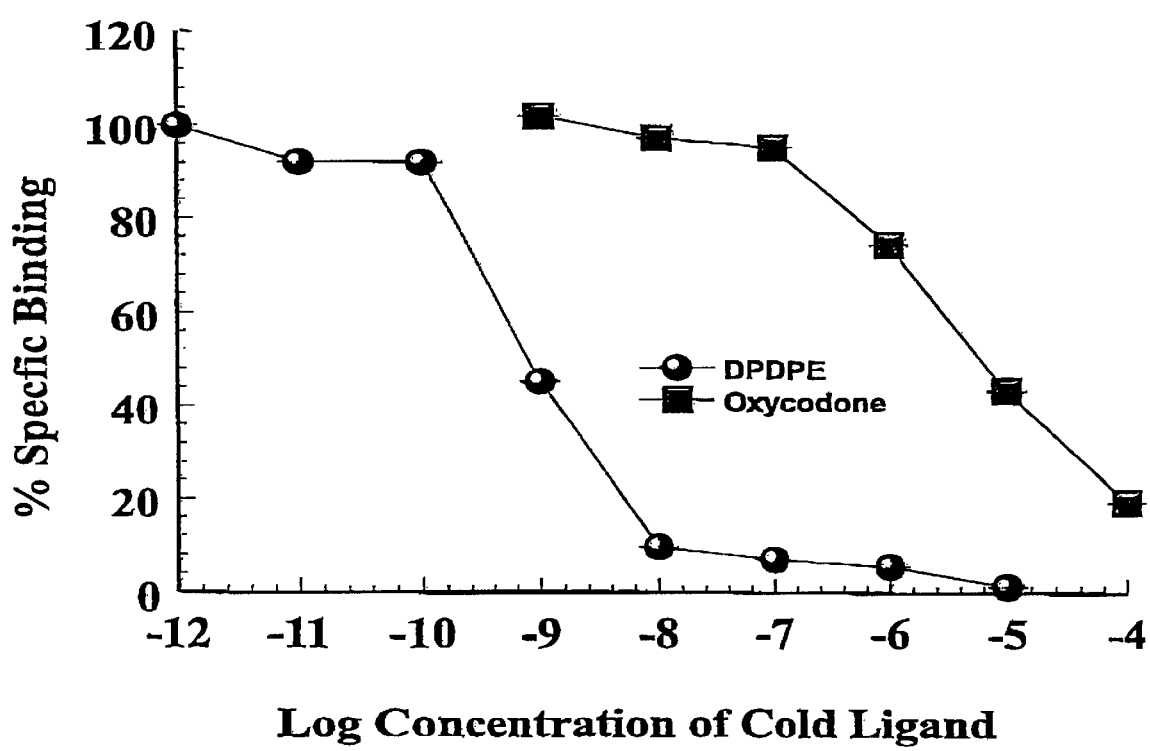
FIG. 8 refers to representative displacement curves of oxycodone and DPDPE against $^3$H-DPDPE-Cl in rat brain membranes.

In $\delta$-opioid receptor binding assays, oxycodone (in concentrations less than 1 $\mu$M) was unable to displace the selective $\delta$-opioid receptor ligand, [$^3$H]DPDPE-Cl (FIG. 8), whereas unlabelled DPDPE displaced [$^3$H]DPDPE with high affinity ($K_D$=1.4 nM), in agreement with values reported in the literature (Raynor et al., 1994, Mol-Pharmacol., 45, 330–334).

Figure 9:
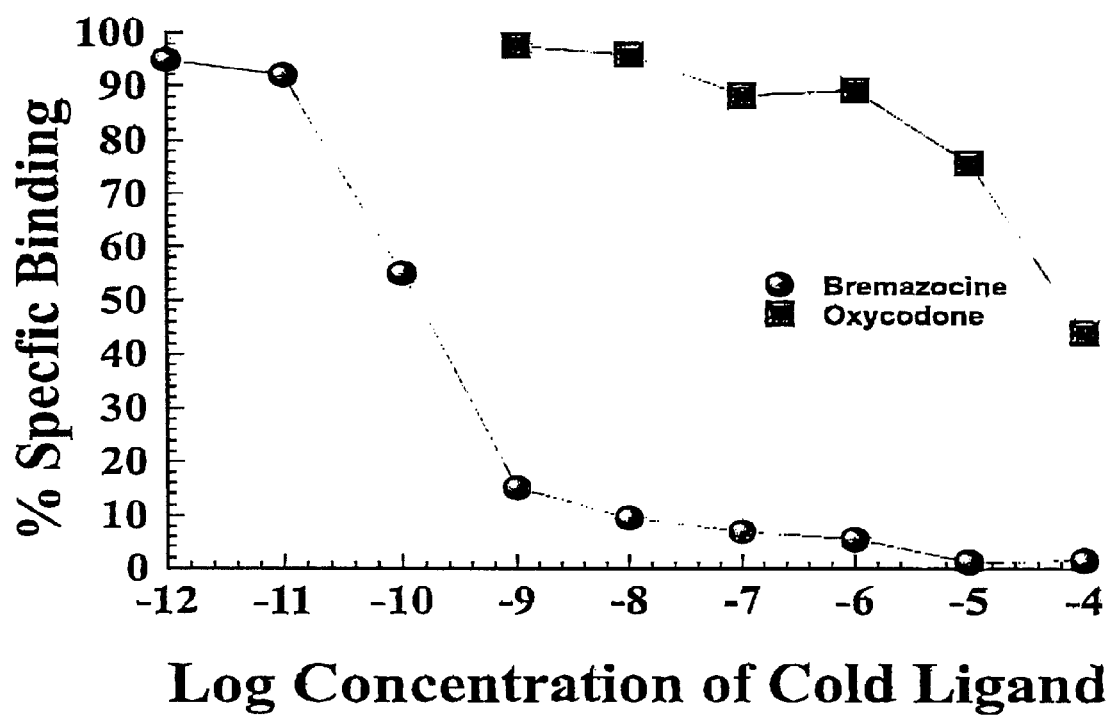
FIG. 9 refers to representative displacement curves of oxycodone and bremazocine against $^3$H-U69,593 in guinea-pig brain membranes.

Similarly oxycodone did not displace [$^3$H]U69,593 (selective $\kappa_1$-opioid receptor ligand) in rat brain membrane preparations to any significant extent ($K_i$>100 $\mu$M), but the ratio of total binding to non-specific binding (NSB) was relatively poor (typically 2:1) due to the low expression of $\kappa_1$-opioid receptors in rat brain. Therefore additional experiments were performed in guinea-pig brain (a tissue in which $\kappa_1$-opioid receptors are highly expressed such that the ratio of total binding to NSB is 10:1) homogenate to further investigate whether oxycodone binds significantly to $\kappa_1$-opioid receptors. Again, oxycodone was unable to displace [$^3$H]U69,593 at concentrations less than 100 $\mu$M (FIG. 9), indicating that oxycodone does not bind significantly to $\kappa_1$-opioid receptors. Bremazocine, a universal opioid receptor ligand ($\mu$, $\delta$, $\kappa_1$- and $\kappa_2$-ligands) served as the positive control in that it displaced [$^3$H]U69,593 with a similar affinity ($K_i$=0.4 nM) to that reported in the literature (Rothman et al., 1990, Peptides, 11, 311–331).

DISCUSSION

The results of our binding experiments presented herein support the findings of our whole animal experiments, described in Example 2, that showed that oxycodone does not elicit its intrinsic antinociceptive effects by interacting with the $\mu$-opioid receptor system.

These whole animal experiments also showed that the selective $\kappa$-opioid receptor antagonist, nor-BNI completely attenuated the antinociceptive effects of i.c.v. oxycodone, whilst having no effect on the antinociceptive effects of i.c.v morphine. Currently, 3 major subtypes of $\kappa$-opioid receptors have been identified, viz, $\kappa_1$, $\kappa_2$ and $\kappa_3$ with nor-BNI binding to only the $\kappa_1$, and $\kappa_2$ subtypes (Takemori et al., 1988, supra; Ni et al., 1996, supra). As oxycodone did not displace [$^3$H]U69,593 (selective $\kappa_1$-agonist) from either rat or guinea-pig brain homogenate to any significant extent ($K_i$>100 $\mu$M), these experiments indicate that oxycodone does not bind to $\kappa_1$-opioid receptors and thus $\kappa_1$-opioid receptors do not mediate oxycodone's intrinsic antinociceptive effects. Thus, when the results of our whole animals experiments (Example 2) are taken together with those of our binding experiments, they strongly suggest that oxycodone is a selective $\kappa_2$-opioid receptor agonist. Further evidence supporting this conclusion is obtained from our observations that (i) the potency and (ii) the antinociceptive profile of i.c.v. oxycodone more closely resemble the respective attributes of i.c.v. administered bremazocine (primarily elicits its antinociceptive effects through $\kappa_2$-opioid receptors) than i.c.v. administered U69,593 (selective $\kappa_1$-opioid agonist) (Example 2).

Additional studies in the literature (Ni et al., 1993, 1995, supra) indicate that the $\kappa_2$-opioid receptor itself comprises 4 discrete subtypes, viz $\kappa_{2a-1}$, $\kappa_{2a-2}$, $\kappa_{2b-1}$ and $\kappa_{2b-2}$ and that the selective $\kappa$-opioid receptor antagonist, nor-BNI, binds with high affinity ($K_i$=5.9 nM) to only the $\kappa_{2a-2}$ subtype in addition to $\kappa_1$-opioid receptors (Ni et al., 1993, supra). As we have now shown that oxycodone does not bind to $\kappa_1$-opioid receptors to any appreciable extent, these results suggest that oxycodone mediates its pain-relieving effects by binding to the $\kappa_{2a-2}$ subtype of $\kappa_2$-opioid receptors. However, as there are no specific ligands for the $\kappa_{2a-2}$ opioid receptor currently available, it is not possible as yet to directly determine oxycodone's binding affinity for this subtype of the $\kappa_2$-opioid receptor.

EXAMPLE 4

Investigation of the Antinociceptive Effects of a Range of Subanalgesic Dosing Combinations of Morphine and Oxycodone Following Subcutaneous Administration to Dark Agouti Rats The studies described in Example 1 showed that co-administration of subanalgesic doses of morphine and oxycodone by both the intracerebroventricular (i.c.v.) route to Sprague-Dawley (SD) rats and by the intraperitoneal (i.p.) route to Dark Agouti (DA) rats elicits marked antinociceptive synergy characterized by a significant increase in both the extent and duration of antinociception when compared with the expected levels of antinociception had only additive antinociceptive effects been achieved. Opioids are not administered by the i.p. route to humans. Rather, the subcutaneous (s.c.) route is the preferred systemic route of opioid drug administration for patients that have difficulty swallowing or that have intractable nausea and vomiting. Therefore, this study was designed to determine (i) the individual doses of morphine or oxycodone administered by the s.c. route to Dark Agouti rats that evoked half-maximal antinociception (the $ED_{50}$ doses) (ii) the $ED_{50}$ doses for a range of s.c. dosing combinations of morphine and oxycodone, (iii) the optimal s.c. dosing combination of morphine plus oxycodone to produce antinociceptive synergy in DA rats and (iv) the magnitude of the synergistic effect produced by the optimum s.c. dosing combination of morphine plus oxycodone to DA rats.

MATERIALS AND METHODS

Materials

Oxycodone hydrochloride was a generous gift from Boots Australia Pty Ltd (Sydney, Australia) Morphine hydrochloride was purchased from Royal Brisbane Hospital Pharmacy (Brisbane, Australia). Medical grade $CO_2$ and $O_2$ were purchased from BOC Gases Australia Ltd (Brisbane, Australia). Tail flick latencies were measured using a Columbus Instruments Tail Flick Analgesia Meter (Columbus Instruments, Ohio, USA).

Animals

Ethical approval for this study was obtained from the Animal Experimentation Ethics Committee of The University of Queensland. Adult male Dark Agouti rats (7–8 weeks of age) were obtained from the Central Animal Breeding House, The University of Queensland. Rats were housed at 21° C. with 12 h/12 h light/dark cycle and with food and water available ad libitum. At the time of experimentation, rats weighed 209±20 g (mean±SD, n=218).

Tail Flick Experimental Procedure

Baseline tail flick latencies (Predrug latencies) were the mean of at least three measurements taken approximately 5 min apart, prior to dosing. Rats were then lightly anesthetized using a (50:50) mixture of $CO_2/O_2$ and then 200 µL of drug solution was injected subcutaneously at the base of neck using a 250 µL glass Hamilton syringe. Tail flick latencies were measured at 10, 20, 30, 45, 60, 90 and 120 min following s.c. injection. The maximum tail flick latency was restricted to 9.0 s to minimise tail tissue damage. The righting reflex, landing reflex and eye reflex of the rat (Poyhia R. and Kalso E., 1992, supra) were tested immediately following the 30, 60 and 120 min tail flick latency measurements.

Drug Dosing

This study was separated into two experimental Cohorts. Rats in Cohort One received s.c. injections of either morphine, oxycodone or vehicle (normal saline) in order to determine the $ED_{50}$ doses for single s.c. injections of morphine or oxycodone. Rats in Cohort Two received s.c. injections of either normal saline (controls), or a combination of morphine and oxycodone in three dosing ratios (morphine:oxycodone), viz. 25:75, 50:50, or 75:25 relative to the $ED_{50}$ doses of single injections of either morphine or oxycodone, determined in Cohort One experiments.

Doses of morphine and oxycodone, alone and in combination, or vehicle (normal saline) were prepared in sterile saline for a total injection volume of 200 µL (Table 1). Eight replicate solutions of each of morphine and/or oxycodone doses were prepared. Following preparation, drug dosing solutions were coded by a member of the research laboratory who was not involved in this study, such that all doses were administered to DA rats in a randomized and double-blind manner. Samples were stored at −20° C., and thawed prior to administration.

Data Analysis

Raw tail flick latencies were converted to the percentage maximum possible effect (%MPE) by the equation shown in Example 1.

For each drug solution administered, the area under the %MPE versus time curve (AUC) was calculated using the trapezoidal rule, with any negative %MPE values arbitrarily assigned a value of zero, The mean (±SEM) percentage maximum AUC (% Max. AUC) for each morphine and/or oxycodone dose was calculated by expressing the mean of the eight AUC values as a percentage of the maximum achievable AUC. The mean (±SEM) % Max. AUC for each morphine and/or oxycodone dose was plotted verses the respective drug dose to produce the individual Dose-Response curves. The Richards' sigmoidal algorithm (Curve Expert®, Microsoft) was fitted to the Dose-Response curve, and the $ED_{50}$ dose (mean±SEM) for each morphine and/or oxycodone dosing combination was determined by interpolation as the dose corresponding to % Max. AUC=50%.

Statistical Analysis

Data were analysed for significant differences using the unpaired Wilcoxon Rank-Sum test. The statistical significance criterion was $p<0.05$.

RESULTS

Cohort One: s.c. injection of single doses of either morphine or oxycodone

Figure 10:
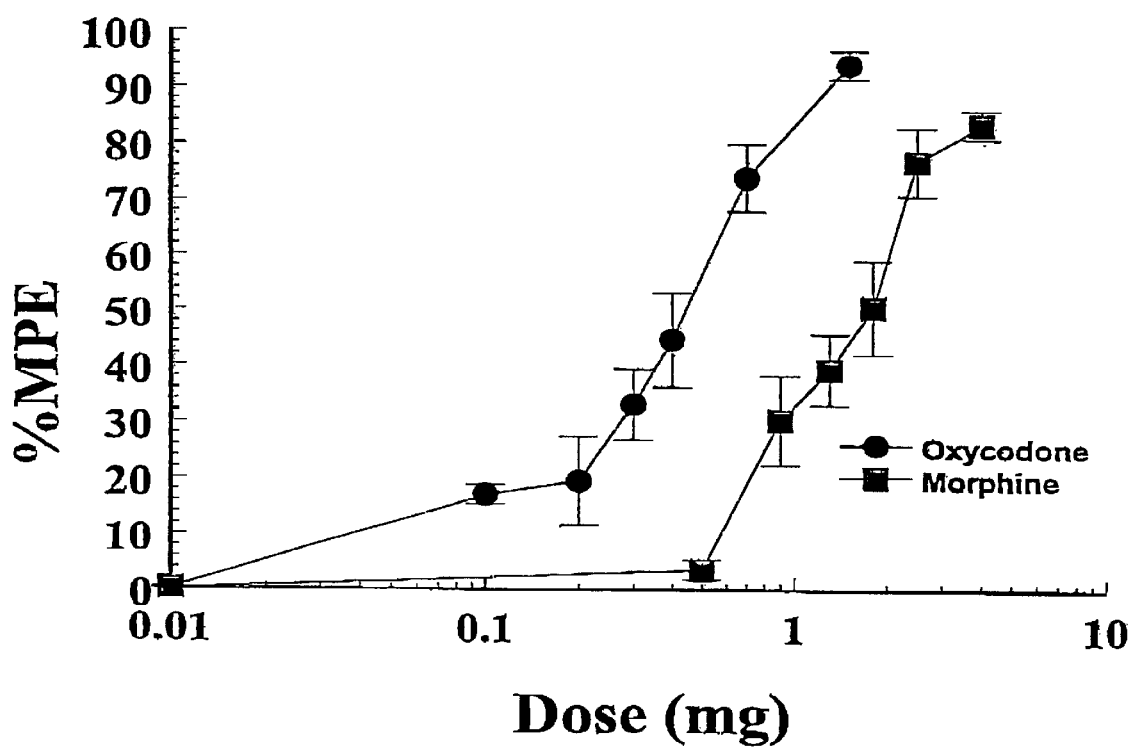
FIG. 10 refers to dose response curves respectively for single s.c. doses of morphine and oxycodone.
Figure 11:
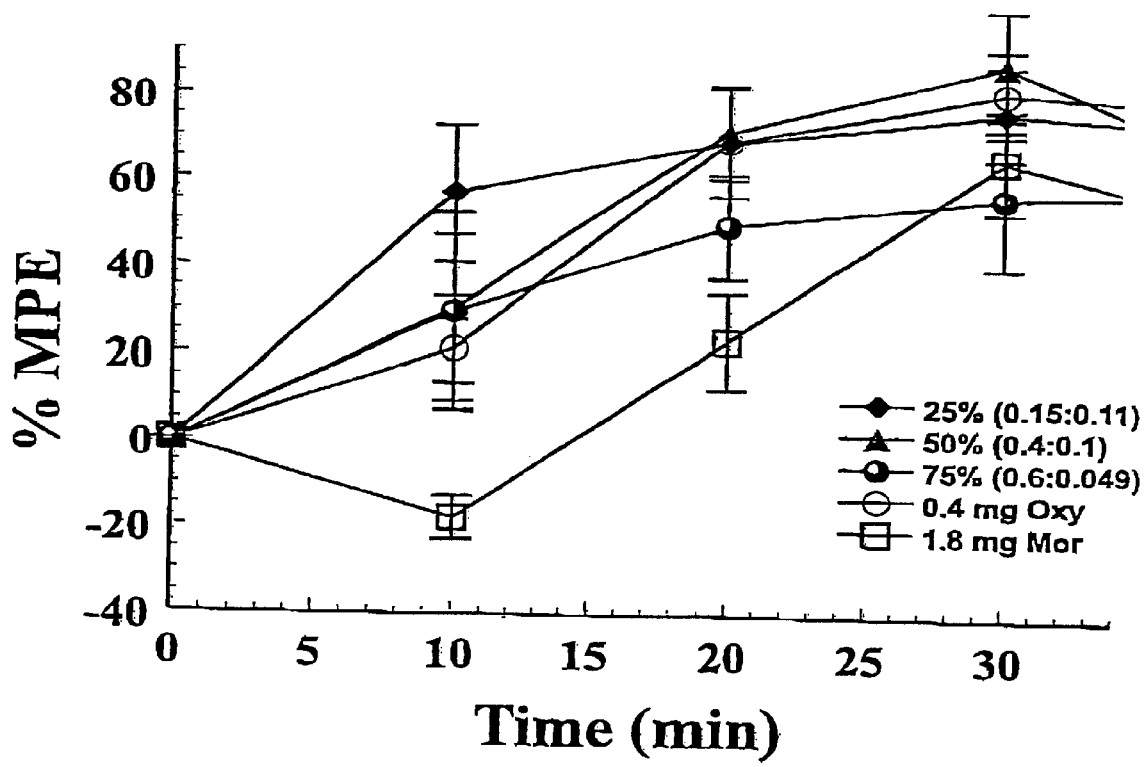
FIG. 11 refers to plots of %MPE. as a function of time to demonstrate onset of antinociception for various ratios of morphine in combination with oxycodone.
Figure 12:
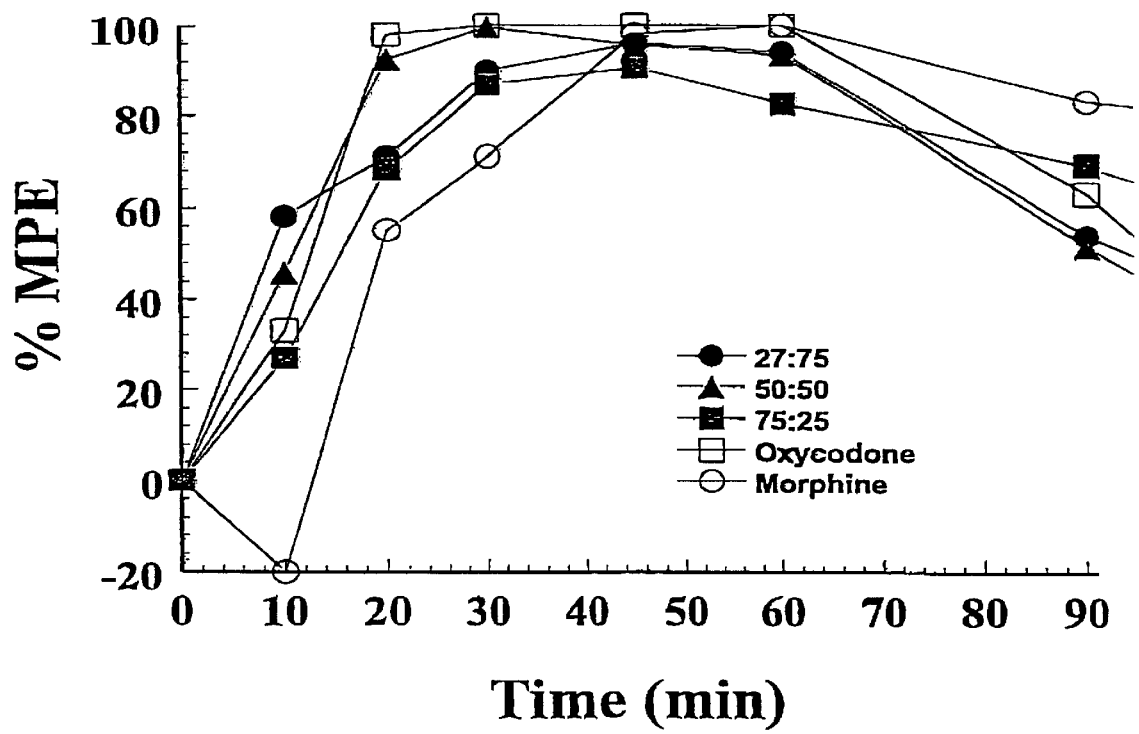
FIG. 12 refers to plots of %MPE as a function of time to demonstrate $T_{max}$; i.e., the time at which combinations of morphine and oxycodone, in various ratios, achieve maximal effect.

The mean AUC for control rats (n=8) that received injections of vehicle (normal saline) was very small (0.2% of the maximum AUC achievable), indicating that no significant antinociception resulted from either the injection procedure itself or the tail flick testing procedure. The mean (±SEM) % Max. AUC achieved following single s.c. injections of morphine or oxycodone are presented in Table 2. The mean (±SEM) $ED_{50}$ doses for single s.c. injections of either morphine or oxycodone determined from the Dose-Response curves (FIG. 10) were 1.8 (±0.2) mg and 0.44 (±0.04) mg, respectively. A plot of the mean (±SEM) %MPE versus time curve following s.c. administration of approximately equipotent doses of morphine and oxycodone is shown in FIGS. 11 and 12. It is readily apparent that although equipotent doses of morphine and oxycodone were administered, the time of onset of antinociception (defined here as %MPE≧30%) and the time to achieve maximum antinociception ($T_{max}$) are more rapid for oxycodone (12 min and 20 min, respectively) than for morphine (22 min and 45 min, respectively).

Behaviorally, rats that received single s.c. injections of either morphine or oxycodone in doses that were greater than the $ED_{50}$ doses, were markedly sedated compared with control rats that received s.c. injections of normal saline. When doses approximating the $ED_{50}$ dose of s.c. morphine (1.8 mg) or oxycodone (0.4 mg) were administered, the rats failed the eye reflex test approximately 40% of the time, but there was no loss of the righting or landing reflexes. At higher s.c. doses of morphine (4.0 mg) or oxycodone (1.5 mg) rats failed the righting reflex test approximately 33% and 50% of the time, respectively. There was no loss of the landing reflex following s.c. administration of any of the single doses of morphine or oxycodone investigated.

Cohort Two: s.c. injection of combined doses of morphine and oxycodone

Figure 13:
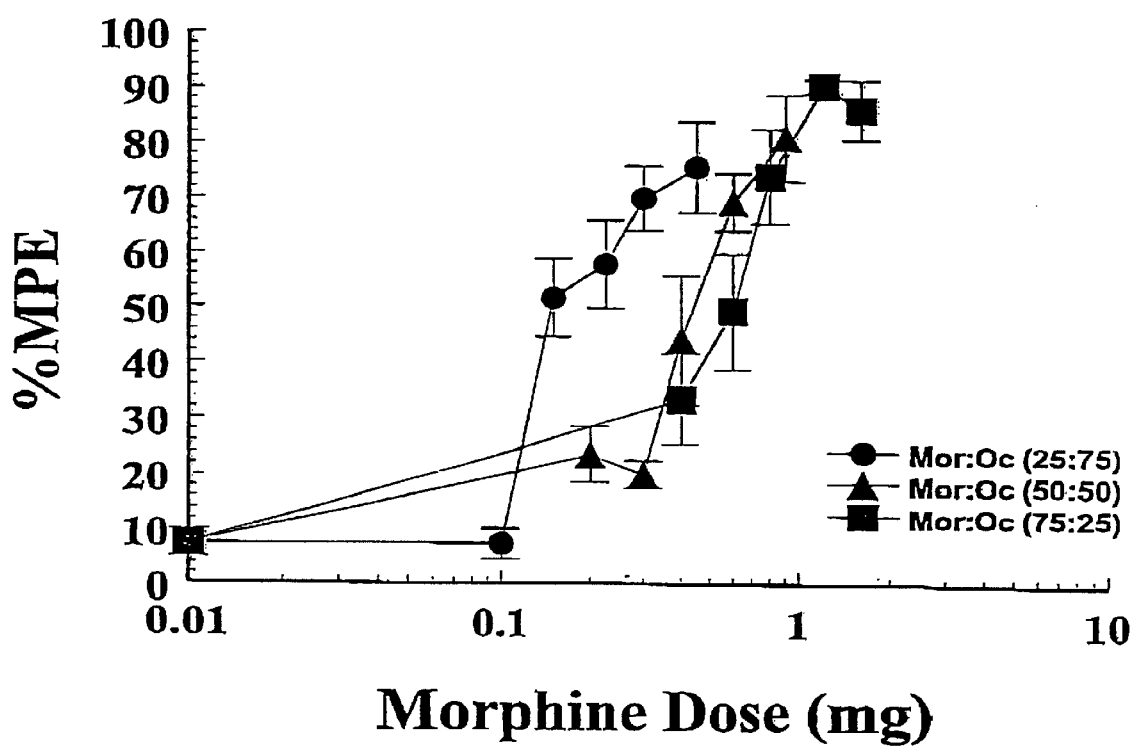
FIG. 13 refers to Dose-Response curves for s.c. doses of morphine in combination with oxycodone in ratios of 25:75, 50;50, and 75:25.
Figure 14:
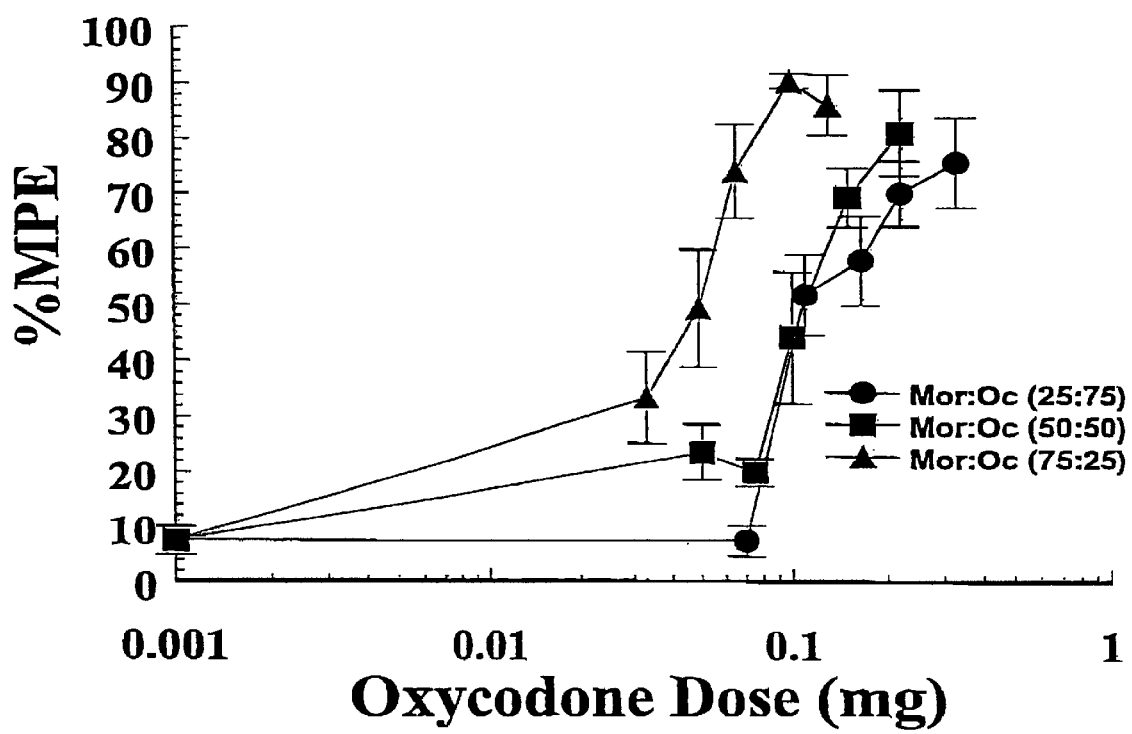
FIG. 14 shows Dose-Response curves of morphine in combination with oxycodone in ratios of 25:75, 50:50, and 75:25.

Control rats in Cohort 2 achieved levels of antinociception such that the mean AUC values achieved was small (7.4% of the maximum AUC achievable). The % Max. AUC values for each morphine:oxycodone dosing combination are presented in Table 3. The Dose-Response curves for these ratios, shown in FIGS. 13 and 14, give the following mean (±SEM) $ED_{50}$ doses for each of the morphine:oxycodone dosing combinations investigated, viz. 0.15 (±0.10) mg: 0.110 (±0.008) mg, 0.46 (±0.07) mg: 0.115 (±0.004) mg and 0.55 (±0.05) mg: 0.049 (±0.0025) mg, for the 25:75, 50:50 and 75:25 dosing ratios, respectively (Table 4). The time of onset of antinociception and the time to achieve maximum antinociception ($T_{max}$) for each of the dosing combinations are shown in Table 5 and FIGS. 11 and 12. These data clearly show that the dosing combination comprising morphine:oxycodone in the ratio 25:75 produced the fastest onset (5 min), while the 50:50 ratio and the oxycodone administered alone had the shortest time required to achieve maximum antinociception ($T_{max}$=20 min).

Figure 15:
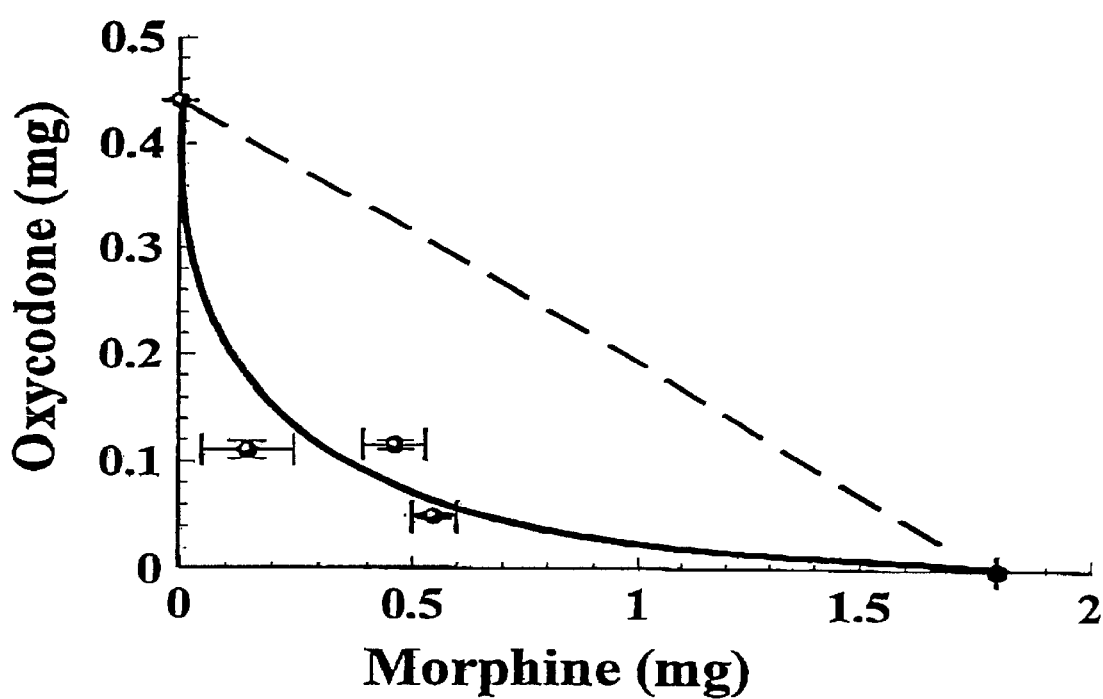
FIG. 15 refers to an isobologram of s.c. dosing combinations of oxycodone and morphine.

Examination of the isobologram (FIG. 15) shows that antinociceptive synergy was obtained following s.c. injection of combined doses of morphine plus oxycodone as the $ED_{50}$ doses determined experimentally for each of the morphine:oxycodone dosing combinations examined were significantly less (p<0.05) than the respective values expected if only additive antinociceptive effects had been observed (shown in the isobologram (FIG. 15) as a dotted straight line joining the $ED_{50}$ doses of s.c. injections of morphine or oxycodone alone). It is also readily apparent from the isobologram (FIG. 15) that in terms of maximum synergistic effect achieved for the lowest overall dose of opioid administered and the shortest time required to achieve onset of antinociception, the optimum morphine:oxycodone dosing combination is that comprising 25:75 of the $ED_{50}$ doses of morphine plus oxycodone This optimum combination of subanalgesic doses of morphine plus oxycodone represented a 12-fold reduction in the morphine dose relative to a single s.c. injection of morphine alone and a 4-fold reduction in the oxycodone dose relative to a single s.c. injection of oxycodone alone that would be required to achieve similar levels of antinociception in DA rats.

In contrast to rats in Cohort One, some rats in Cohort Two that received combination doses of morphine plus oxycodone such that a maximal degree of anticiceptlon was observed were behaviourally indistinguishable from control rats that received s.c. injections of normal saline, in that there were no apparent signs of sedation, respiratory depression or any other adverse opioid side-effects. Additionally, rats in Cohort Two were similar to rats in Cohort One in that there was no loss of the landing reflex following s.c. administration of any of the dosing combinations investigated. However, in contrast to rats in Cohort One, rats in Cohort Two did not lose their righting reflex even after administration of the highest combination doses of morphine plus oxycodone such that maximum antinociception was achieved for the majority of the 2 h study period. When doses approximating the $ED_{50}$ values for each of the morphine:oxycodone combinations were administered, there was no significant loss of the eye reflex for rats receiving the 75:25 dosing ratio (0.6:0.049 mg), whilst the rats receiving the 50:50 dosing ratio (0.4:0.1 mg) had a similar incidence of eye reflex loss to rats in Cohort One. Rats that received the 25:75 dosing ratio (0.15, 0.11 mg) had a lower incidence of eye reflex loss than found for rats in Cohort One.

DISCUSSION

Studies described in Example 1 have shown that marked antinociceptive synergy (assessed using the tail flick latency test) is produced following i.c.v. co-administration of subanalgesic doses of morphine plus oxycodone to SD rats. However, as adult male SD rats avidly metabolize systemically administered oxycodone to its potent analgesically active, O-demethylated metabolite, oxymorphone (=10-fold more potent than morphine) and humans do not (Ross et al., 1993, supra; Lacouture et al., 1996, J. Pharmacol. Exp. Ther., 266, 926–933), it was essential that our subsequent studies investigating whether antinociceptive synergy occurred following systemic co-administration of subanalgesic doses of morphine plus oxycodone were performed in an animal model where O-demethylation of oxycodone to oxymorphone occurred to a low extent (Cleary et al., 1994, supra), in a manner similar to humans (Ross et al., 1993, supra; Lacouture et al., 1996, supra). Hence, DA rats were chosen for these studies as they are genetically deficient in the enzyme required to O-demethylate oxycodone to oxymorphone (Cleary et al., 1994, supra). When subanalgesic doses of morphine plus oxycodone were systemically co-administered to DA rats by the i.p. route, marked antinociceptive synergy was observed (see Example 1). However, in humans, the s.c. route rather than the i.p. route is the preferred systemic route of opioid drug administration for patients that have difficulty swallowing or that have intractable nausea and vomiting. Therefore, the marked antincocieptive synergy observed in the studies described herein (FIG. 15) where DA rats received s.c. co-administration of three different subanalgesic dosing combinations of morphine plus oxycodone are very exciting in terms of their potential applicability to the enhanced management of moderate to severe pain in humans.

Close examination of the isobologram (FIG. 15) reveals that the optimum dosing combination comprised a 12-fold reduction in the morphine dose and a 4-fold reduction in the oxycodone dose compared with the s.c. doses of morphine plus oxycodone that would have been required to produce similar levels of antinociception had only additive antinociception occurred. Importantly, the marked antinociceptive synergy observed in our studies following s.c. co-administration of subanalgesic doses of morphine plus oxycodone was not due to motor deficits as rats did not lose their righting or landing reflexes even when the highest combined s.c. doses were administered. When this finding is combined with the additional observation that the incidence of sedation was reduced in these rats compared with rats receiving equipotent single s.c. doses of either morphine or oxycodone, our results indicate that it may be possible to achieve profound analgesia in humans with a reduced incidence of undesirable opioid side-effects (sedation, respiratory depression) by co-administering appropriate subanalgesic doses of morphine plus oxycodone.

In their guidelines for the relief of cancer pain, the World Health Organization (WHO) recommends that cancer pain be managed by administering the drugs recommended on each rung of the analgesic ladder and that strong opioids such as morphine and oxycodone, should not be co-administered (WHO, 1986, supra). However, our current studies strongly suggest that co-administration of subanalgesic doses of the strong opioids, morphine and oxycodone, may be beneficial in that it may allow patients to have very good analgesia whilst decreasing the incidence of unpleasant opioid side-effects. Our findings of antinociceptive synergy between oxycodone and morphine also conflict with the statement commonly found in the literature (Mather, L. E., 1995, Clin, Exp. Pharmacol. Physiol., 22, 833–836) that all clinically used opioid drugs elicit their pain-relieving effects through the same receptor mechanism as morphine. However, if this statement were true, we would have observed additive and not synergistic levels of antinociception, particularly following i.c.v. co-administration of subanalgesic doses of morphine plus oxycodone where the intrinsic effects of the drugs administered would have determined the absolute levels of antinociception observed.

Importantly, our previously published studies (Leow, K. P. and Smith, M. T., 1994, supra) showed that oxycodone is an opioid agonist in that its intrinsic antinociceptive effects were completely attenuated by i.c.v. administration of the nonselective opioid antagonist, naloxone. Studies described herein (Example 2) involving i.c.v. administration of the selective $\mu_1$, $\delta$- and $\kappa$-opioid receptor antagonists, naloxonazine, naltrindole and nor-binaltorphimine (nor-BNI), respectively, prior to the i.c.v. administration of oxycodone have shown that oxycodone's antinociceptive effects were attenuated only by nor-BNI, indicating that oxycodone appears to be a selective $\kappa$-opioid receptor agonist. Although there are three major subtypes of $\kappa$-opioid receptor, viz. $\kappa_1$, $\kappa_2$ and $\kappa_3$, nor-BNI has been reported to bind only to $\kappa_1$ and $\kappa_2$-opioid receptors (Takemori et al., 1988, supra; Ni et al., 1996, supra) but not $\kappa_3$-opioid receptors (Koch et al., 1992, Brain Res., 581, 311–314). Combining this information with the results of our recent brain homogenate binding studies (Example 3 herein) that showed that oxycodone does not bind appreciably ($K_i>100$ $\mu$M) to $\kappa_1$-opioid receptors suggests that oxycodone's intrinsic antinociceptive effects are mediated through $\kappa_2$-opioid receptors. Thus, it is highly likely that the antinociceptive synergy observed following co-administration of subanalgesic doses of morphine plus oxycodone is mediated through a mechanism involving a $\mu$-$\kappa_2$ synergistic interaction of opioid receptors in the CNS. Given that it has been reported previously that antinociceptive synergy may be produced following supraspinal administration of a $\mu$-opioid agonist such as morphine together with intrathecal administration of a $\kappa_1$-opioid agonist such as U50,488H (Sutters et al., 1990, supra), it is certainly plausible that the synergistic antinociceptive effects observed following s.c. co-administration of subanalgesic doses of morphine plus oxycodone, are mediated by a $\mu$-$\kappa_2$ synergistic interaction of opioid receptors in the CNS.

EXAMPLE 5

Preliminary Investigation of the Antinociceptive Effects of Hydromorphone and Fentanyl in Subanalgesic Dosing Combinations with Oxycodone Following Subcutaneous Administration to Dark Agouti Rats The above studies have shown that co-administration of subanalgesic doses of morphine and oxycodone by both the intracerebroventricular (i.c.v.) route to Sprague-Dawley (SD) rats and by the intraperitoneal (i.p.) route and subcutaneous (s.c.) route to Dark Agouti (DA) rats elicits marked antinociceptive synergy characterized by a significant increase in both the extent and duration of antinociception when compared with the expected levels of antinociception had only additive antinociceptive effects been achieved. A proposed mechanism for this synergistic effect involves the interaction between $\mu$-$\kappa_2$ opioid receptors. If this hypothesis is true then antinociceptive synergy may occur when other $\mu$-opioid agonists are administered in combination with oxycodone. Accordingly, this study was designed to investigate if the $\mu$-opioid agonists hydromorphone and fentanyl in subanalgesic dosing combinations with oxycodone could produce antinociceptive synergy in Dark Agouti (DA) rats by the s.c. route of administration.

MATERIALS AND METHODS

Materials

Oxycodone hydrochloride was a generous gift from Boots Australia Pty Ltd (Sydney, Australia). Fentanyl hydrochloride and hydromorphone hydrochloride were supplied by Sigma-Aldrich (Sydney, Australia). Medical grade $CO_2$ and $O_2$ were purchased from BOC Gases Australia Ltd (Brisbane, Australia). Tail flick latencies were measured using a Columbus Instruments Tail Flick Analgesia Meter (Columbus Instruments, Ohio, USA).

Animals

Ethical approval for this study was obtained from the Animal Experimentation Ethics Commnittee of The University of Queensland. Adult male Dark Agouti rats (7–8 weeks of age) were obtained from the Central Animal Breeding House, The University of Queensland. Rats were housed at 21° C. with 12 h/12 h light/dark cycle and with food and water available ad libitum.

Expermental Procedure

Baseline tail flick latencles (Predrug latencies) were the mean of at least three measurements taken approximately 5 min apart, prior to dosing. Rats were lightly anaesthetized using a (50:50) mixture of $CO_2/O_2$ and then 200 $\mu$L of drug solution was injected subcutaneously at the base of neck using a 250 $\mu$L glass Hamilton syringe. Tail flick latencies were measured at 10, 20, 30, 45, 60, 90 and 120 min following s.c. injection. The maximum tail flick latency was restricted to 9.0 s to minimize tail tissue damage.

Subanalgesic doses of each of fentanyl and hydrormorphone were determined, and then administered with subanalgesic doses of oxycodone (0.15 mg).

Data Analysis

Raw tail flick latencies were converted to the percentage maximum possible effect (%MPE) as previously described (Example 1).

RESULTS

The AUC value achieved after dosing DA rats with 0.15 mg oxycodone was 11%. The AUC of this dose was not significantly different from that of injections of saline in control rats (p>0.05).

Figure 16:
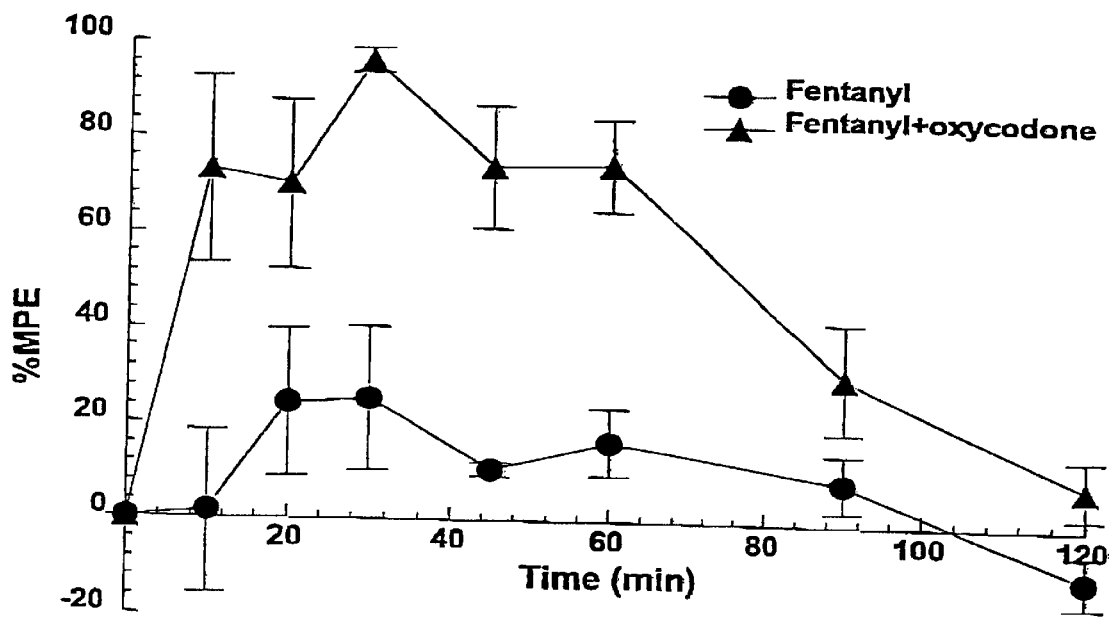
FIG. 16 shows the degree of antinociception (%MPE) as a function of time following s.c. administration to Dark Agouti rats of: 0.01 mg fentanyl in combination with 0.15 mg oxycodone; and 0.01 mg fentanyl solus.
Figure 17:
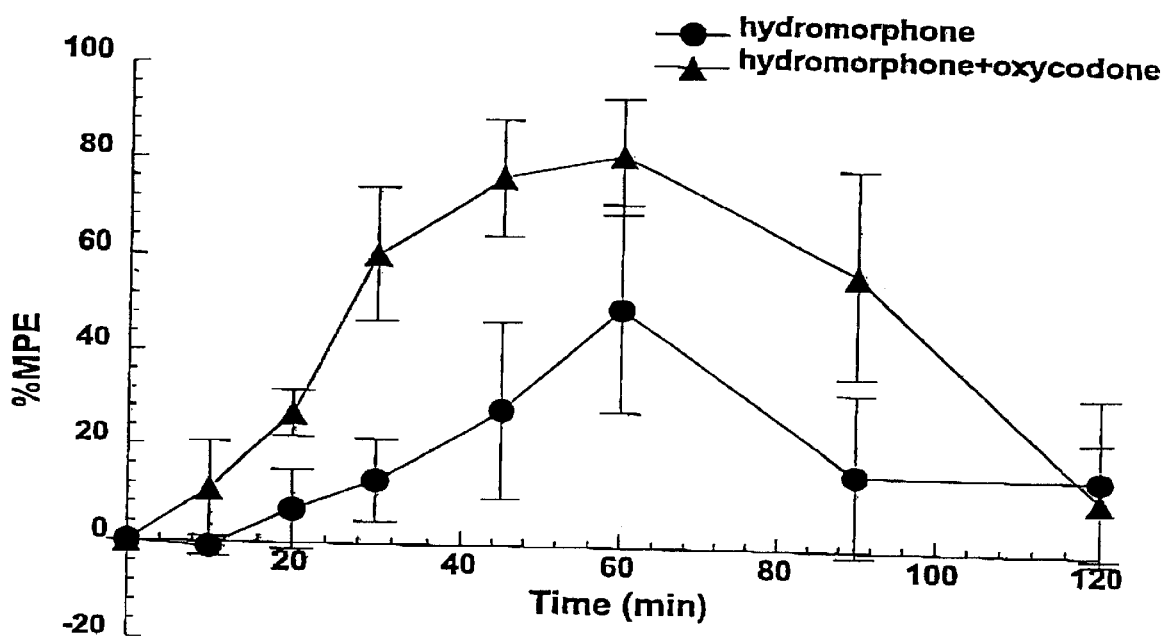
FIG. 17 shows the degree of antinociception (%MPE) as a function of time following s.c. administration to Dark Agouti rats of: 0.1 mg hydromorphone in combination with 0.15 mg oxycodone; and 0.1 mg hydromorphone solus.

When administered in combination with oxycodone (0.15 mg), hydromorphone (0.1 mg) (FIG. 16) and fentanyl (0.015 mg) (FIG. 17) displayed levels of antinociception significantly higher than that attained by the addition of the antinociceptive levels of each drug administered alone.

DISCUSSION

Our studies described herein have shown that subanalgesic doses of morphine and oxycodone when administered in combination via i.c.v., i.p. (Example 1) and s.c. (Example 4) routes of administration produce a synergistic antinociceptive effect. The mechanism for this synergistic effect has been proposed to involve the interaction of $\mu$-(morphine) and $\kappa_2$ (oxycodone) opioid receptors. In a preliminary investigation of this mechanism, the above studies reveal that subcutaneous administration into DA rats of subanalgesic doses of two potent $\mu$-opioid receptor agonists (fentanyl and hydromorphone) respectively in combination with a subanalgesic dose of oxycodone results in the production of antinociceptive synergy. Accordingly, these results support the $\mu$-$\kappa_2$ synergistic mechanism of the invention.

EXAMPLE 6

Human Trials of Combined Dosing with Subanalgesic Doses of Morphine Plus Oxycodone Preliminary results of a human clinical trial currently underway in surgical patients indicate that co-administration of oxycodone plus morphine by the intravenous (i.v.) route elicits synergistic clinical responses. For example, co-injection of sub-therapeutic doses of morphine (2.0 mg) plus oxycodone (2.0 mg) enabled intubation of patients at induction of anesthesia. When oxycodone or morphine are administered by the i.v. route alone, doses of approximately 10 mg are used for intubation. Additionally the combination of subanalgesic doses of morphine plus oxycodone had a very rapid onset (within 5 min) of clinical effect in a manner similar to 10 mg (i.v.) doses of oxycodone alone and in contrast to morphine alone which is characterized by a slow onset of maximum clinical response (30 min).

In terms of total opioid consumption to achieve satisfactory pain relief by patients in the 48 h study period immediately following surgery, our preliminary data indicate a reduction in total opioid requirements of approximately 2-fold.

These preliminary human results showing synergistic clinical responses in patients dosed with a combination of subanalgesic doses of morphine plus oxycodone are consistent with our observations in experimental animals and are consistent with many previous studies which have shown that in terms of opioid action, rats are an appropriate model of the human.

In summary, the perceived advantages of the synergistic formulations of the invention include (i) the alleviation of pain in a patient by administering significantly lower doses of a $\mu$- or a $\kappa_2$-opioid than would otherwise be required if these opioids were administered individually; and (ii) reducing the incidence of adverse opioid side-effects herein described.

TABLE 1

Dose of Morphine and/or Oxycodone Administered (in 200 µl Dosing Volume*)

| Cohort One | | Cohort Two | | |
|---|---|---|---|---|
| Morphine | Oxycodone | Morphine (mg) Oxycodone (mg) | | |
| (mg) | (mg) | 25:75 | 50:50 | 75:25 |
| 0.0 | 0.0 | 0.000:0.000 | 0.0:0.000 | 0.0:0.000 |
| 0.5 | 0.1 | 0.100:0.070 | 0.2:0.050 | 0.4:0.033 |
| 0.9 | 0.2 | 0.150:0.110 | 0.3:0.075 | 0.6:0.049 |
| 1.3 | 0.3 | 0.225:0.165 | 0.4:0.100 | 0.8:0.065 |
| 1.8 | 0.4 | 0.300:0.220 | 0.6:0.150 | 1.2:0.098 |
| 2.5 | 0.7 | 0.450:0.330 | 0.9:0.220 | 1.6:0.130 |
| 4.0 | 1.5 | | | |

TABLE 2

% Max. AUC Values for Morphine and Oxycodone Doses (Cohort One)

| Morphine | % Max AUC | | Oxycodone | % Max AUC | |
|---|---|---|---|---|---|
| (mg) | Mean | SEM | (mg) | Mean | SEM |
| 0 | 0.2% | 0.2% | 0 | 0.2% | 0.2% |
| 0.5 | 3.5% | 1.8% | 0.1 | 1.7% | 0.5% |
| 0.9 | 30.2% | 7.9% | 0.2 | 19.4% | 5.8% |
| 1.3 | 39.2% | 6.3% | 0.3 | 33.0% | 4.7% |
| 1.8 | 50.3% | 8.4% | 0.4 | 44.5% | 9.1% |
| 2.5 | 76.7% | 6.0% | 0.7 | 73.8% | 3.9% |
| 4.0 | 83.4%; | 2.5% | 1.5 | 94.0% | 2.2% |

TABLE 3

% Max. AUC Values for Morphine (Mor) and Oxycodone (Oxy) Combination Doses (Cohort Two)

| Mor:Oxy 25:75 | | | Mor:Oxy 50:50 | | | Mor:Oxy 75:25 | | |
|---|---|---|---|---|---|---|---|---|
| Mor:Oxy | % Max. AUC | | Mor:Oxy | % Max. AUC | | Mor:Oxy | % Max. AUC | |
| (mg) | Mean | SEM | (mg) | Mean | SEM | (mg) | Mean | SEM |
| 0.000:0.000 | 7.4% | 2.5% | 0.0:0.000 | 7.4% | 2.5% | 0.0:0.000 | 7.4% | 2.5% |
| 0.100:0.070 | 7.4% | 2.7% | 0.2:0.050 | 23.5% | 5.0% | 0.4:0.033 | 33.3% | 8.1% |
| 0.150:0.110 | 51.6% | 4.6% | 0.3:0.075 | 19.9% | 2.6% | 0.6:0.049 | 49.2% | 10.5% |
| 0.225:0.165 | 57.8% | 8.0% | 0.4:0.100 | 44.0% | 11.7% | 0.8:0.065 | 73.9% | 8.6% |
| 0.300:0.220 | 69.7% | 5.9% | 0.6:0.150 | 69.2% | 5.3% | 1.2:0.098 | 90.3% | 1.5% |
| 0.450:0.330 | 75.6% | 8.2% | 0.9:0.220 | 80.9% | 7.8% | 1.6:0.130 | 86/0% | 5.4% |

TABLE 4

$ED_{50}$ Doses for Morphine and Oxycodone

| Mor Oxy | Mor $ED_{50}$ (mg) | | Mor $ED_{50}$ (mg) | |
|---|---|---|---|---|
| Ratio | Mean | SEM | Mean | SEM |
| 0:100 | 0 | 0 | 0.44 | 0.04 |
| 25:75 | 0.15 | 0.10 | 0.110 | 0.008 |
| 50:50 | 0.46 | 0.07 | 0.115 | 0.004 |
| 75:25 | 0.55 | 0.05 | 0.049 | 0.003 |
| 100:0 | 1.8 | 0.2 | 0 | 0.00 |

TABLE 5

Time of Onset of Antinociception* and Time to Achieve Maximum Antinociception ($T_{max}$)

| Mor Oxy Ratio | Onset (min)* | $T_{max}$ (min) |
|---|---|---|
| 0:100 | 12 | 20 |
| 25:75 | 5 | 30 |
| 50:50 | 10 | 20 |
| 75:25 | 10 | 30 |
| 100:0 | 22 | 45 |

LEGENDS

TABLE 1

Control rats received s.c. injections of normal saline

TABLE 5

Onset of antinociception is defined here as %MPE>30% estimated from FIG. 11.

FIG. 1A

Degree of antinociception (%MPE) as a function of time following i.c.v. administration to Sprague-Dawley rats of: 40 nmol oxycodone in combination with 15 nmol morphine -●-; 40 nmol oxycodone solus -▼-.

FIG. 1B

Degree of antinociception (%MPE) as a function of time following i.c.v. administration to Sprague-Dawley rats of: 15 nmol morphine solus -⊟-.

FIG. 2A

Degree of antinociception (%MPE) as a function of time following i.p. administration to Dark Agouti rats of: 571 nmol oxycodone in combination with 621 nmol morphine -●-; 571 nmol oxycodone solus -▼-.

FIG. 2B

Degree of antinociception (%MPE) as a function of time following i.p. administration to Dark Agouti rats of: 621 nmol morphine solus -⊟-.

FIG. 3

Degree of antinociception observed following i.c.v. administration of (A) oxycodone (200 nmol), (B) morphine (78 nmol).

FIG. 4

Degree of antinocicepfion observed following i.c.v. administration of the $\mu_1$-selective opioid receptor antagonist naloxonazine (1 nmol) 24 h prior to i.c.v. administration of (A) oxycodone (200 nmol) and (B) morphine (78 nmol). Control data for oxycodone and morphine are shown in FIG. 3.

FIG. 5

Degree of antinociception observed following i.c.v administration of the δ-selective opioid antagonist, naltrindole (1 nmol) administered 15 min prior to oxycodone (200 nmol) or DPDPE (45 nmol). Control data for oxycodone are shown in FIG. 3.

FIG. 6

Degree of antinociception observed following nor-BNI (0.3 nmol) administration 24 h prior to i.c.v. administration of (A) oxycodone (200 nmol), (B) U69,593 (133 nmol), (control data for U69,593 (133 nmol i.c.v.) in untreated rats is also shown), (C) bremazocine (57 nmol) and (D) morphine (78 nmol). See FIG. 3 for oxycodone and morphine control data.

FIG. 7

Representative displacement curves of oxycodone and morphine against $^3$H-morphine in rat membranes. The $K_d$ of morphine was determined to be 1.2 nM, while oxycodone displayed a moderately low $K_i$ of 349 nM.

FIG. 8

Representative displacement curves of oxycodone and DPDPE against $^3$H-DPDPE-Cl in rat membranes. Oxycodone was unable to displace the δ-opioid agonist at concentrations below 1 $\mu$M, indicating that the affinity of oxycodone for δ-opioid receptors is far too low for it to be an agonist at this site.

FIG. 9

Representative displacement curves of oxycodone and bremazocine against $^3$H-U69,593 in rat membranes. Oxycodone was unable to displace the $\kappa_1$-opioid agonist at concentrations below 10 $\mu$M, indicating that oxycodone cannot be an agonist at the $\kappa_1$-opioid receptor.

FIG. 10

Dose-Response curve for single s.c. doses of morphine and oxycodone. $ED_{50}$ doses (mean±SEM) were determined as 1.8 (±0.2) mg morphine and 0.44 (±0.04) mg oxycodone.

FIG. 11

Plots of % MPE versus time for 2.5 mg morphine, 0.7 mg oxycodone, 0.3 mg: 0.22 mg, 0.6 mg: 0.15 mg and 1.2 mg: 0.098 mg morphone oxycodone, demonstrating onset of antinociception (defined as % MPE≧30%) estimated at 22, 12, 5, 10 and 10 min, respectively.

FIG. 12

Plots of % MPE versus time for 2.5 mg morphine, 0.7 mg oxycodone, 0.3 mg: 0.22 mg, 0.6 mg: 0.15 mg and 1.2 mg: 0.098 mg (morphine:oxycodone), demonstrating time to maximum antinociception ($T_{max}$) of 45, 20, 30, 20 and 30 min, respectively.

FIG. 13

Morphine Dose-Response curve for s.c. doses of morphine and combined morphine plus oxycodone in ratios 25:75, 50:50 and 75:25 (morphine:oxycodone), demonstrating $ED_{50}$ morphine doses of 1.8 (±0.2) mg, 0.15 (±0.10) mg, 0.46 (±0.07) mg and 0.55 (±0.05) mg, respectively.

FIG. 14

Oxycodone Dose-Response curve for s.c. doses of oxycodone and combined morphine plus oxycodone in ratios 25:75, 50:50 and 75:25 (morphine:oxycodone), demonstrating $ED_{50}$ oxycodone doses of 0.44 (±0.04) mg, 0.110 (±0.008) mg, 0.115 (±0.004) mg and 0.049 (±0.003) mg, respectively.

FIG. 15

Isobologram of morphine (mg) versus oxycodone (mg). Significant antinociceptive synergy is indicated (p<0.05) by solid line. (Dotted straight line indicates additive antinociception).

FIG. 16

Degree of antinocicepfion (%MPE) as a function of time following s.c. administration to Dark Agouti rats of: 0.01 mg fentanyl in combination with 0.15 mg oxycodone; and 0.01 mg fentanyl solus.

FIG. 17

Degree of antinociception (%MPE) as a function of time following s.c. administration to Dark Agouti rats of: 0.1 mg hydromorphone in combination with 0.15 mg oxycodone; and 0.1 mg hydromorphone solus.

What is claimed is:

1. An analgesic composition comprising a sub-analgesic dosage of a $\mu$-opioid agonist selected from the group consisting of morphine, fentanyl, sufentanil, alfentanil and hydromorphone, or a pharmaceutically acceptable salt thereof, and a sub-analgesic dosage of oxycodone which is a $\kappa_2$-opioid agonist or a pharmaceutically acceptable salt thereof.

2. An analgesic composition as claimed in claim 1 wherein the $\mu$-opioid agonist is in the form of a pharmaceutically acceptable salt.

3. An analgesic composition as claimed in claim 1 wherein the $\mu$-opioid agonist is morphine.

4. An analgesic composition as claimed in claim 1 wherein the $\mu$-opioid agonist is fentanyl.

5. An analgesic composition as claimed in claim 1 wherein the $\mu$-opioid agonist is hydromorphone.

6. An analgesic composition as claimed in claim 1 wherein the oxycodone is in the form of a pharmaceutically acceptable salt.

7. An analgesic composition as claimed in claim 3 wherein an initial sub-analgesic dosage of morphine for a human adult through an intracerebroventricular route is between about 0.05 mg and about 0.25 mg per day.

8. An analgesic composition as claimed in claim 3 wherein an initial sub-analgesic dosage of morphine for a human adult through a subcutaneous, intravenous, intramuscular, buccal or sublingual route is between about 0.5 mg and about 3.5 mg every four hours.

9. An analgesic composition as claimed in claim 8 wherein the initial sub-analgesic dosage of morphine is between about 0.5 mg and about 3.0 mg every four hours.

10. An analgesic composition as claimed in claim 8 wherein the initial sub-analgesic dosage of morphine is between about 0.5 mg and about 2.5 mg every four hours.

11. An analgesic composition as claimed in claim 8 wherein the initial sub-analgesic dosage is between about 0.5 mg and about 2.0 mg every four hours.

12. An analgesic composition as claimed in claim 3 wherein an initial sub-analgesic dosage of morphine, in controlled-release dosage form, for a naive human adult through a subcutaneous, intravenous, intramuscular, buccal or sublingual route is between about 1.5 mg and about 10.5 mg every 12 hours.

13. An analgesic composition as claimed in claim 12 wherein the initial sub-analgesic dosage of morphine is between about 1.5 mg and about 9.0 mg every 12 hours.

14. An analgesic composition as claimed in claim 12 wherein the initial sub-analgesic dosage of morphine is between about 1.5 mg and about 7.5 mg every 12 hours.

15. An analgesic composition as claimed in claim 12 wherein the initial sub-analgesic dosage of morphine is between about 1.5 mg and about 6.0 mg every 12 hours.

16. An analgesic composition as claimed in claim 3 wherein an initial sub-analgesic dosage of morphine, in controlled-release dosage form, for a naive human adult through a subcutaneous, intravenous, intramuscular, buccal or sublingual route is between about 3.0 mg and about 21.0 mg every 24 hours.

17. An analgesic composition as claimed in claim 16 wherein the initial sub-analgesic dosage of morphine is between about 3.0 mg and about 18.0 mg every 24 hours.

18. An analgesic composition as claimed in claim 16 wherein the initial sub-analgesic dosage of morphine is between about 3.0 mg and about 15.0 mg every 24 hours.

19. An analgesic composition as claimed in claim 16 wherein the initial sub-analgesic dosage of morphine is between about 3.0 mg and about 12.0 mg every 24 hours.

20. An analgesic composition as claimed in claim 3 wherein an initial sub-analgesic dosage of morphine for a naive human adult through an oral or rectal route is between about 2.0 mg and about 25.0 mg every four hours.

21. An analgesic composition as claimed in claim 20 wherein the initial sub-analgesic dosage of morphine is between about 5.0 mg and about 20.0 mg every four hours.

22. An analgesic composition as claimed in claim 20 wherein the initial sub-analgesic dosage of morphine is between about 5.0 mg and about 15.0 mg every four hours.

23. An analgesic composition as claimed in claim 3 wherein an initial sub-analgesic dosage of morphine, in controlled-release dosage form, for a naive human adult through an oral or rectal route is between about 6.0 mg and about 75.0 mg every 12 hours.

24. An analgesic composition as claimed in claim 23 wherein the initial sub-analgesic dosage of morphine is between about 15.0 mg and about 60.0 mg every 12 hours.

25. An analgesic composition as claimed in claim 3 wherein an initial sub-analgesic dosage of morphine, in controlled-release dosage form, for a naive human adult through an oral or rectal route is between about 12.0 mg and about 150.0 mg every 24 hours.

26. An analgesic composition as claimed in claim 25 wherein the initial sub-analgesic dosage of morphine is between about 30.0 mg and about 120.0 mg every 24 hours.

27. An analgesic composition as claimed in claim 25 wherein the initial sub-analgesic dosage of morphine is between about 30.0 mg and about 90.0 mg every 24 hour.

28. An analgesic composition as claimed in claim 3 wherein an initial sub-analgesic dosage of morphine for a human child through an intracerebroventricular route is between about 0.05 mg and about 0.25 mg per day.

29. An analgesic composition as claimed in claim 3 wherein an initial sub-analgesic dosage of morphine for a naive human child through a subcutaneous route is between about 0.01 mg/kg and about 0.09 mg/kg every four hours.

30. An analgesic composition as claimed in claim 3 wherein an initial sub-analgesic dosage of morphine for a naive human child through an intravenous route is between about 0.01 mg/kg and about 0.04 mg/kg every four hours.

31. An analgesic composition as claimed in claim 3 wherein an initial sub-analgesic dosage of morphine for a naive human child through an oral or rectal route is between about 0.1 mg/kg and about 0.4 mg/kg ever four hours.

32. An analgesic composition as claimed in claim 3 wherein an initial sub-analgesic dosage of morphine for a naive lower animal through an oral or parenteral route is between about 0.5 mg/kg and about 5 mg/kg every three to six hours.

33. An analgesic composition as claimed in claim 6 wherein an initial sub-analgesic dosage of oxycodone for a human adult through an intracerebroventricular route is between about 0.05 mg and about 0.25 mg per day.

34. An analgesic composition as claimed in claim 6 wherein an initial sub-analgesic dosage of oxycodone for a naive human adult through a subcutaneous or intravenous route is between about 1.0 mg and about 8.0 mg every four hours.

35. An analgesic composition as claimed in claim 34 wherein the initial sub-analgesic dosage of oxycodone is between about 1.0 mg and about 6.0 mg every four hours.

36. An analgesic composition as claimed in claim 34 wherein the initial sub-analgesic dosage of oxycodone is between about 1.0 mg and about 4.0 mg every four hours.

37. An analgesic composition as claimed in claim 6 wherein an initial sub-analgesic dosage of oxycodone, in controlled-release dosage form, for a naive human adult through a subcutaneous or intravenous route is between about 3.0 mg and about 24.0 mg every 12 hours.

38. An analgesic composition as claimed in claim 37 wherein the initial sub-analgesic dosage of oxycodone is between about 3.0 mg and about 18.0 mg every 12 hours.

39. An analgesic composition as claimed in claim 37 wherein the initial sub-analgesic dosage of oxycodone is between about 3.0 mg and about 12.0 mg every 12 hours.

40. An analgesic composition as claimed in claim 6 wherein an initial sub-analgesic dosage of oxycodone, in controlled-release dosage form, for a naive human adult through a subcutaneous or intravenous route is between about 6.0 mg and about 48.0 mg every 24 hours.

41. An analgesic composition as claimed in claim 40 wherein the initial sub-analgesic dosage of oxycodone is between about 6.0 mg and about 36.0 mg every 24 hours.

42. An analgesic composition as claimed in claim 40 wherein the initial sub-analgesic dosage of oxycodone is between about 6.0 mg and about 24.0 mg every 24 hours.

43. An analgesic composition as claimed in claim 6 wherein an initial sub-analgesic dosage of oxycodone for a naive human adult through an oral or rectal route is between about 1.0 mg and about 8.0 mg every four hours.

44. An analgesic composition as claimed in claim 43 wherein the initial sub-analgesic dosage of oxycodone is between about 1.0 mg and about 6.0 mg every four hours.

45. An analgesic composition as claimed in claim 43 wherein the initial sub-analgesic dosage of oxycodone is between about 1.0 mg and about 4.0 mg every four hours.

46. An analgesic composition as claimed in claim 6 wherein an initial sub-analgesic dosage of oxycodone, in controlled-release dosage form, for a naive human adult through an oral or rectal route is between about 3.0 mg and about 24.0 mg every 12 hours.

47. An analgesic composition as claimed in claim 46 wherein the initial sub-analgesic dosage of oxycodone is between about 3.0 mg and about 18.0 mg every 12 hours.

48. An analgesic composition as claimed in claim 46 wherein the initial sub-analgesic dosage of oxycodone is between about 3.0 mg and about 12.0 mg every 12 hours.

49. An analgesic composition as claimed in claim 6 wherein an initial sub-analgesic dosage of oxycodone, in controlled-release dosage form, for a naive human adult through an oral or rectal route is between about 6.0 mg and about 48.0 mg every 24 hours.

50. An analgesic composition as claimed in claim 49 wherein the initial sub-analgesic dosage of oxycodone is between about 6.0 mg and about 36.0 mg every 24 hours.

51. An analgesic composition as claimed in claim 49 wherein the initial sub-analgesic dosage of oxycodone is between about 6.0 mg and about 24.0 mg every 24 hours.

52. An analgesic composition as claimed in claim 6 wherein an initial sub-analgesic dosage of oxycodone for a human child through an intracerebroventnicuiar route is between about 0.05 mg and about 0.25 mg per day.

53. An analgesic composition as claimed in claim 6 wherein an initial sub-analgesic dosage of oxycodone for a naive human child through a subcutaneous or intravenous route is between about 0.01 mg/kg and about 0.08 mg/kg every four hours.

54. An analgesic composition as claimed in claim 53 wherein the initial sub-analgesic dosage of oxycodone is between about 0.01 mg/kg and about 0.06 mg/kg every four hours.

55. An analgesic composition as claimed in claim 53 wherein the initial sub-analgesic dosage of oxycodone is between about 0.01 mg/kg and about 0.04 mg/kg every four hours.

56. An analgesic composition as claimed in claim 6 wherein an initial sub-analgesic dosage of oxycodone, in controlled-release dosage form, for a naive human child through a subcutaneous or intravenous route is between about 0.03 mg/kg and about 0.24 mg/kg every 12 hours.

57. An analgesic composition as claimed in claim 56 wherein the initial sub-analgesic dosage of oxycodone is between about 0.03 mg/kg and about 0.18 mg/kg every 12 hours.

58. An analgesic composition as claimed in claim 56 wherein the initial sub-analgesic dosage of oxycodone is between about 0.03 mg/kg and about 0.12 mg/kg every 12 hours.

59. An analgesic composition as claimed in claim 6 wherein an initial sub-analgesic dosage of oxycodone, in controlled-release dosage form, for a naive human child through a subcutaneous or intravenous route is between about 0.06 mg/kg and about 0.48 mg/kg every 24 hours.

60. An analgesic composition as claimed in claim 59 wherein the initial sub-analgesic dosage of oxycodone is between about 0.06 mg/kg and about 0.36 mg/kg every 24 hours.

61. An analgesic composition as claimed in claim 59 wherein the initial sub-analgesic dosage of oxycodone is between about 0.06 mg/kg and about 0.24 mg/kg every 24 hours.

62. An analgesic composition as claimed in claim 6 wherein an initial sub-analgesic dosage of oxycodone for a naive human child through an oral or rectal route is between about 0.01 mg/kg and about 0.08 mg/kg every four hours.

63. An analgesic composition as claimed in claim 62 wherein the initial sub-analgesic dosage of oxycodone is between about 0.02 mg/kg and about 0.06 mg/kg every four hours.

64. An analgesic composition as claimed in claim 62 wherein the initial sub-analgesic dosage of oxycodone is between about 0.02 mg/kg and about 0.04 mg/kg every four hours.

65. An analgesic composition as claimed in claim 6 wherein an initial sub-analgesic dosage of oxycodone, in controlled-release dosage form, for a naive human child through an oral or rectal route is between about 0.03 mg/kg and about 0.24 mg/kg every 12 hours.

66. An analgesic composition as claimed in claim 65 wherein the initial sub-analgesic dosage of oxycodone is between about 0.06 mg/kg and about 0.18 mg/kg every 12 hours.

67. An analgesic composition as claimed in claim 65 wherein the initial sub-analgesic dosage of oxycodone is between about 0.06 mg/kg and about 0.12 mg/kg every 12 hours.

68. An analgesic composition as claimed in claim 6 wherein an initial sub-analgesic dosage of oxycodone, in controlled-release dosage form, for a naive human child through an oral or rectal route is between about 0.06 mg/kg and about 0.48 mg/kg every 24 hours.

69. An analgesic composition as claimed in claim 68 wherein the initial sub-analgesic dosage of oxycodone is between about 0.12 mg/kg and about 0.36 mg/kg every 24 hours.

70. An analgesic composition as claimed in claim 68 wherein the initial sub-analgesic dosage of oxycodone is between about 0.12 mg/kg and about 0.24 mg/kg every 24 hours.

71. An analgesic composition as claimed in claim 6 wherein an initial sub-analgesic dosage of oxycodone for a naive lower animal through an oral or parenteral route is between about 0.1 mg/kg and about 5 mg/kg every three to six hours.

72. A method for producing analgesia in humans and lower animals which comprises administering concurrently to a human or lower animal in need of such treatment a composition comprising a sub-analgesic dosage of a $\mu$-opioid agonist selected from the group consisting of morphine, fentanyl, sufentanil, alfentanil and hydromorphone, or a pharmaceutically acceptable salt thereof, and a sub-analgesic dosage of oxycodone which is a $\kappa_2$-opioid agonist or a pharmaceutically acceptable salt thereof.

73. A method as claimed in claim 72 wherein the $\mu$-opioid agonist is in the form of a pharmaceutically acceptable salt.

74. A method as claimed in claim 72 wherein the $\mu$-opioid agonist is morphine.

75. A method as claimed in claim 72 wherein the $\mu$-opioid agonist is fentanyl.

76. A method as claimed in claim 72 wherein the μ-opioid agonist is hydromorphone.

77. A method as claimed in claim 72 wherein the oxycodone is in the form of a pharmaceutically acceptable salt.

78. A method as claimed in claim 74 wherein an initial sub-analgesic dosage of morphine for a human adult through an intracerebroventricular route is between 0.05 mg and about 0.25 mg per day.

79. A method as claimed in claim 74 wherein an initial sub-analgesic dosage of morphine for a human adult through a subcutaneous, intravenous, intramuscular, buccal or sublingual route is between about 0.5 mg and about 3.5 mg every four hours.

80. A method as claimed in claim 79 wherein the initial sub-analgesic dosage of morphine is between about 0.5 mg and about 3.0 mg every four hours.

81. A method as claimed in claim 79 wherein the initial sub-analgesic dosage of morphine is between about 0.5 mg and about 2.5 mg every four hours.

82. A method as claimed in claim 79 wherein the initial sub-analgesic dosage of morphine is between about 0.5 mg and about 2.0 mg every four hours.

83. A method as claimed in claim 74 wherein an initial sub-analgesic dosage of morphine, in controlled-release dosage form, for a naive human adult through a subcutaneous, intravenous, intramuscular, buccal or sublingual route is between about 1.5 mg and about 10.5 mg every 12 hours.

84. A method as claimed in claim 83 wherein the initial sub-analgesic dosage of morphine is between about 1.5 mg and about 9.0 mg every 12 hours.

85. A method as claimed in claim 83 wherein the initial sub-analgesic dosage of morphine is between about 1.5 mg and about 7.5 mg every 12 hours.

86. A method as claimed in claim 83 wherein the initial sub-analgesic dosage of morphine is between about 1.5 mg and about 6.0 mg every 12 hours.

87. A method as claimed in claim 74 wherein an initial sub-analgesic dosage of morphine, in controlled-release dosage form, for a naive human adult through a subcutaneous, intravenous, intramuscular, buccal or sublingual route is between about 3.0 mg and about 21.0 mg every 24 hours.

88. A method as claimed in claim 87 wherein the initial sub-analgesic dosage of morphine is between about 3.0 mg and about 18.0 mg every 24 hours.

89. A method as claimed in claim 88 wherein the initial sub-analgesic dosage of morphine is between about 3.0 mg and about 15.0 mg every 24 hours.

90. A method as claimed in claim 87 wherein the initial sub-analgesic dosage of morphine is between about 3.0 mg and about 12.0 mg every 24 hours.

91. A method as claimed in claim 74 wherein an initial sub-analgesic dosage of morphine for a naive human adult through an oral or rectal route is between about 2.0 mg and about 25.0 mg every four hours.

92. A method as claimed in claim 91 wherein the initial sub-analgesic dosage of morphine is between about 5.0 mg and about 20.0 mg every four hours.

93. A method as claimed in claim 91 wherein the initial sub-analgesic dosage of morphine is between about 5.0 mg and about 15.0 mg every four hours.

94. A method as claimed in claim 74 wherein an initial sub-analgesic dosage of morphine, in controlled-release dosage form, for a naive human adult through an oral or rectal route is between about 6.0 mg and about 75.0 mg every 12 hours.

95. A method as claimed in claim 94 wherein the initial sub-analgesic dosage of morphine is between about 15.0 mg and about 60.0 mg every 12 hours.

96. A method as claimed in claim 74 wherein an initial sub-analgesic dosage of morphine, in controlled-release dosage form, for a naive human adult through an oral or rectal route is between about 12.0 mg and about 150.0 mg every 24 hours.

97. A method as claimed in claim 96 wherein the initial sub-analgesic dosage of morphine is between about 30.0 mg and about 120.0 mg every 24 hours.

98. A method as claimed in claim 96 wherein the initial sub-analgesic dosage of morphine is between about 30.0 mg and about 90.0 mg every 24 hours.

99. A method as claimed in claim 74 wherein an initial sub-analgesic dosage of morphine for a human child through an intracerebroventricular route is between about 0.05 mg and about 0.25 mg per day.

100. A method as claimed in claim 74 wherein an initial sub-analgesic dosage of morphine for a naive human child through a subcutaneous route is between about 0.01 mg/kg and about 0.09 mg/kg every four hours.

101. A method as claimed in claim 74 wherein an initial sub-analgesic dosage of morphine for a naive human child through an intravenous route is between about 0.01 mg/kg and about 0.04 mg/kg every four hours.

102. A method as claimed in claim 74 wherein an initial sub-analgesic dosage of morphine for a naive human child through an oral, transdermal or rectal route is between about 0.1 mg/kg and 0.4 mg/kg every four hours.

103. A method as claimed in claim 74 wherein an initial sub-analgesic dosage of morphine for a naive lower animal through an oral or parenteral route is between about 0.5 mg/kg and about 5 mg/kg every three to six hours.

104. A method as claimed in claim 77 wherein an initial sub-analgesic dosage of oxycodone for a human adult through an intracerebroventricular route is between about 0.05 mg and about 0.25 mg per day.

105. A method as claimed in claim 77 wherein an initial sub-analgesic dosage of oxycodone for a naive human adult through a subcutaneous or intravenous route is between about 1.0 mg and about 8.0 mg every four hours.

106. A method as claimed in claim 105 wherein the initial sub-analgesic dosage of oxycodone is between about 1.0 mg and about 6.0 mg every four hours.

107. A method as claimed in claim 106 wherein the initial sub-analgesic dosage of oxycodone is between about 1.0 mg and about 4.0 mg every four hours.

108. A method as claimed in claim 77 wherein an initial sub-analgesic dosage of oxycodone, in controlled-release dosage form, for a naive human adult through a subcutaneous or intravenous route is between about 3.0 mg and about 24.0 mg every 12 hours.

109. A method as claimed in claim 108 wherein the initial sub-analgesic dosage of oxycodone is between about 3.0 mg and about 18.0 mg every 12 hours.

110. A method as claimed in claim 108 wherein the initial sub-analgesic dosage of oxycodone is between about 3.0 mg and about 12.0 mg every 12 hours.

111. A method as claimed in claim 77 wherein an initial sub-analgesic dosage of oxycodone, in controlled-release dosage form, for a naive human adult through a subcutaneous or intravenous route is between about 6.0 mg and about 48.0 mg every 24 hours.

112. A method as claimed in claim 111 wherein the initial sub-analgesic dosage of oxycodone is between about 6.0 mg and about 36.0 mg every 24 hours.

113. A method as claimed in claim 111 wherein the initial sub-analgesic dosage of oxycodone is between about 6.0 mg and about 24.0 mg every 24 hours.

114. A method as claimed in claim 77 wherein an initial sub-analgesic dosage of oxycodone for a naive human adult through an oral or rectal route is between about 1.0 mg and about 8.0 mg every four hours.

115. A method as claimed in claim 114 wherein the initial sub-analgesic dosage of oxycodone is between about 1.0 mg and about 6.0 mg every four hours.

116. A method as claimed in claim 114 herein the initial sub-analgesic dosage of oxycodone is between about 1.0 mg and about 4.0 mg every four hours.

117. A method as claimed in claim 77 wherein an initial sub-analgesic dosage of oxycodone in controlled-release dosage form, for a naive human adult through an oral or rectal route is between about 3.0 mg and about 24.0 mg every 12 hours.

118. A method as claimed in claim 117 wherein the initial sub-analgesic dosage of oxycodone is between about 3.0 mg and about 18.0 mg every 12 hours.

119. A method as claimed in claim 117 wherein the initial sub-analgesic dosage of oxycodone is between about 3.0 mg and about 12.0 mg every 12 hours.

120. A method as claimed in claim 77 wherein an initial sub-analgesic dosage of oxycodone, in controlled-release dosage form, for a naive human adult through an oral or rectal route is between about 6.0 mg and about 48.0 mg every 24 hours.

121. A method as claimed in claim 120 wherein the initial sub-analgesic dosage of oxycodone is between about 6.0 mg and about 36.0 mg every 24 hours.

122. A method as claimed in claim 120 wherein the initial sub-analgesic dosage of oxycodone is between about 6.0 mg and about 24.0 mg every 24 hours.

123. A method as claimed in claim 77 wherein an initial sub-analgesic dosage of oxycodone for a human child through an intracerebroventricular route is between about 0.05 mg and about 0.25 mg per day.

124. A method as claimed in claim 77 wherein an initial sub-analgesic dosage of oxycodone for a naive human child through a subcutaneous or intravenous route is between about 0.01 mg/kg and about 0.08 mg/kg every four hours.

125. A method as claimed in claim 124 wherein the initial sub-analgesic dosage of oxycodone is between about 0.01 mg/kg and about 0.06 mg/kg every four hours.

126. A method as claimed in claim 124 wherein the initial sub-analgesic dosage of oxycodone is between about 0.01 mg/kg and about 0.04 mg/kg every four hours.

127. A method as claimed in claim 77 wherein an initial sub-analgesic dosage of oxycodone, in controlled-release dosage form, for a naive human child through a subcutaneous or intravenous route is between about 0.03 mg/kg and about 0.24 mg/kg every 12 hours.

128. A method as claimed in claim 127 wherein the initial sub-analgesic dosage of oxycodone is between about 0.03 mg/kg and about 0.18 mg/kg every 12 hours.

129. A method as claimed in claim 127 wherein the initial sub-analgesic dosage of oxycodone is between about 0.03 mg/kg and about 0.12 mg/kg every 12 hours.

130. A method as claimed in claim 77 wherein an initial sub-analgesic dosage of oxycodone, in controlled-release dosage form, for a naive human child through a subcutaneous or intravenous route is between about 0.06 mg/kg and about 0.48 mg/kg every 24 hours.

131. A method as claimed in claim 130 wherein the initial sub-analgesic dosage of oxycodone is between about 0.06 mg/kg and about 0.36 mg/kg every 24 hours.

132. A method as claimed in claim 130 wherein the initial sub-analgesic dosage of oxycodone is between about 0.06 mg/kg and about 0.24 mg/kg every 24 hours.

133. A method as claimed in claim 77 wherein an initial sub-analgesic dosage of oxycodone for a naive human child through an oral or rectal route is between about 0.01 mg/kg and about 0.08 mg/kg every four hours.

134. A method as claimed in claim 133 wherein the initial sub-analgesic dosage of oxycodone is between about 0.02 mg/kg and about 0.06 mg/kg every four hours.

135. A method as claimed in claim 133 wherein the initial sub-analgesic dosage of oxycodone is between about 0.02 mg/kg and about 0.04 mg/kg every four hours.

136. A method as claimed in claim 77 wherein an initial sub-analgesic dosage of oxycodone, in controlled-release dosage form, for a naive human child through an oral or rectal route is between about 0.03 mg/kg and about 0.24 mg/kg every 12 hours.

137. A method as claimed in claim 136 wherein the initial sub-analgesic dosage of oxycodone is between about 0.06 mg/kg and about 0.18 mg/kg every 12 hours.

138. A method as claimed in claim 136 wherein the initial sub-analgesic dosage of oxycodone is between about 0.06 mg/kg and about 0.12 mg/kg every 12 hours.

139. A method as claimed in claim 77 wherein an initial sub-analgesic dosage of oxycodone, in controlled-release dosage form, for a naive human child through an oral or rectal route is between about 0.06 mg/kg and about 0.48 mg/kg every 24 hours.

140. A method as claimed in claim 139 wherein the initial sub-analgesic dosage of oxycodone is between about 0.12 mg/kg and about 0.36 mg/kg every 24 hours.

141. A method as claimed in claim 139 wherein the initial sub-analgesic dosage of oxycodone is between about 0.12 mg/kg and about 0.24 mg/kg every 24 hours.

142. A method as claimed in claim 77 wherein an initial sub-analgesic dosage of oxycodone for a naive lower animal through an oral or parenteral route is between about 0.1 mg/kg and about 5 mg/kg every three to six hours.

143. A method as claimed in claim 72 wherein the mode of administering the composition is selected from the group consisting of oral, rectal, parenteral, sublingual, buccal, intrathecal, epidural, intravenous, intra-articular, intramuscular, intradermal, subcutaneous, inhalational, intraocular, intraperitoneal, intracerebroventricular and transdermal.

144. A method as claimed in claim 72 wherein the sub-analgesic dosage of the $\mu$-opioid agonist or a pharmaceutically acceptable salt thereof and the sub-analgesic dosage of the oxycodone or a pharmaceutically acceptable salt thereof are administered through separate routes of administration.

145. An analgesic composition comprising a sub-analgesic dosage of morphine a derivative of morphine or a pharmaceutically acceptable salt thereof, and a sub-analgesic dosage of oxycodone or a pharmaceutically acceptable salt thereof.

146. An analgesic composition as claimed in claim 145 wherein the sub-analgesic dosage of morphine or the morphine derivative is in the form of a pharmaceutically acceptable salt.

147. An analgesic composition as claimed in claim 145 wherein the sub-analgesic dosage of oxycodone is in the form of a pharmaceutically acceptable salt.

148. An analgesic composition as claimed in claim 145 wherein each of the sub-analgesic dosages of morphine or the morphine derivative and oxycodone is in the form of a pharmaceutically acceptable salt.

149. A method as claimed in claim 144 wherein the μ-opioid agonist is in the form of a pharmaceutically acceptable salt.

150. A method as claimed in claim 144 wherein the oxycodone is in the form of a pharmaceutically acceptable salt.

151. A method for producing analgesia in humans and lower animals which comprises administering concurrently to a human or lower animal in need of such treatment a composition comprising a sub-analgesic dosage of morphine, a derivative of morphine, or a pharmaceutically acceptable salt thereof, and a sub-analgesic dosage of oxycodone or a pharmaceutically acceptable salt thereof.

152. A method as claimed in claim 151 wherein the morphine or the morphine derivative is in the form of a pharmaceutically acceptable salt.

153. A method as claimed in claim 151 wherein the oxycodone is in the form of a pharmaceutically acceptable salt.

154. An analgesic composition comprising a sub-analgesic dosage of morphine or a pharmaceutically acceptable salt thereof, wherein the dosage is selected from the group consisting of:
 (A) an initial sub-analgesic dosage for a human adult through an intracerebroventricular route is between about 0.05 mg and about 0.25 mg per day;
 (B) an initial sub-analgesic dosage for a human adult through a subcutaneous, intravenous, intramuscular, buccal or sublingual route is between about 0.5 mg and about 3.5 mg every four hours;
 (C) an initial sub-analgesic dosage, in controlled-release dosage form, for a naive human adult through a subcutaneous, intravenous, intramuscular, buccal or sublingual route is between about 1.5 mg and about 10.5 mg every 12 hours;
 (D) an initial sub-analgesic dosage, in controlled-release dosage form, for a naive human adult through a subcutaneous, intravenous, intramuscular, buccal or sublingual route is between about 3.0 mg and about 21.0 mg every 24 hours;
 (E) an initial sub-analgesic dosage for a naive human adult through an oral or rectal route is between about 2.0 mg and about 25.0 mg every four hours;
 (F) an initial sub-analgesic dosage, in controlled-release dosage form, for a naive human adult through an oral or rectal route is between about 6.0 mg and about 75.0 mg every 12 hours;
 (G) an initial sub-analgesic dosage, in controlled-release dosage form, for a naive human adult through an oral or rectal route is between about 12.0 mg and about 150.0 mg every 24 hours;
 (H) an initial sub-analgesic dosage for a human child through an intracerebroventricular route is between about 0.05 mg and about 0.25 mg per day
 (I) an initial sub-analgesic dosage for a naive human child through a subcutaneous route is between about 0.01 mg/kg and about 0.09 mg/kg every four hours;
 (J) an initial sub-analgesic dosage of morphine for a naive human child through an intravenous route is between about 0.01 mg/kg and about 0.04 mg/kg every four hours;
 (K) an initial sub-analgesic dosage for a naive human child through an oral or rectal route is between about 0.1 mg/kg and about 0.4 mg/kg every four hours;
 (L) an initial sub-analgesic dosage for a naive lower animal through an oral or parenteral route is between about 0.5 mg/kg and about 5 mg/kg every three to six hours;
 and a sub-analgesic dosage of oxycodone or a pharmaceutically acceptable salt thereof, wherein the dosage is selected from the group consisting of:
 (i) an initial sub-analgesic dosage for a human adult through an intracerebroventricular route is between about 0.05 mg and about 0.25 mg per day;
 (ii) an initial sub-analgesic dosage for a naive human adult through a subcutaneous or intravenous route is between about 1.0 mg and about 8.0 mg every four hours;
 (iii) an initial sub-analgesic dosage, in controlled-release dosage form, for a naive human adult through a subcutaneous or intravenous route is between about 3.0 mg and about 24.0 mg every 12 hours;
 (iv) an initial sub-analgesic dosage, in controlled-release dosage form, for a naive human adult through a subcutaneous or intravenous route is between about 6.0 mg and about 48.0 mg every 24 hours;
 (v) an initial sub-analgesic dosage for a naive human adult through an oral or rectal route is between about 1.0 mg and about 8.0 mg every four hours;
 (vi) an initial sub-analgesic dosage, in controlled-release dosage form, for a naive human adult through an oral or rectal route is between about 3.0 mg and about 24.0 mg every 12 hours;
 (vii) an initial sub-analgesic dosage, in controlled-release dosage form, for a naive human adult through an oral or rectal route is between about 6.0 mg and about 48.0 mg every 24 hours;
 (viii) an initial sub-analgesic dosage for a human child through an intracerebroventricular route is between about 0.05 mg and about 0.25 mg per day;
 (ix) an initial sub-analgesic dosage for a naive human child through a subcutaneous or intravenous route is between about 0.01 mg/kg and about 0.08 mg/kg every four hours;
 (x) an initial sub-analgesic dosage, in controlled-release dosage form, for a naive human child through a subcutaneous or intravenous route is between about 0.03 mg/kg and about 0.24 mg/kg every 12 hours;
 (xi) an initial sub-analgesic dosage, in controlled-release dosage form, for a naive human child through a subcutaneous or intravenous route is between about 0.06 mg/kg and about 0.48 mg/kg every 24 hours;
 (xii) an initial sub-analgesic dosage for a naive human child through an oral or rectal route is between about 0.01 mg/kg and about 0.08 mg/kg every four hours;
 (xiii) an initial sub-analgesic dosage, in controlled-release dosage form, for a naive human child through an oral or rectal route is between about 0.03 mg/kg and about 0.24 mg/kg every 12 hours;
 (xiv) an initial sub-analgesic dosage, in controlled-release dosage form, for a naive human child through an oral or rectal route is between about 0.06 mg/kg and about 0.48 mg/kg every 24 hours; and
 (xv) an initial sub-analgesic dosage for a naive lower animal through an oral or parenteral route is between about 0.1 mg/kg and about 5 mg/kg every three to six hours.

155. A method for producing analgesia in humans and lower animals which comprises administering concurrently to a human or lower animal in need of such treatment a composition comprising a sub-analgesic dosage of morphine or a pharmaceutically acceptable salt thereof, wherein the dosage is selected from the group consisting of:
 (A) an initial sub-analgesic dosage for a human adult through an intracerebroventricular route is between about 0.05 mg and about 0.25 mg per day;

(B) an initial sub-analgesic dosage for a human adult through a subcutaneous, intravenous, intramuscular, buccal or sublingual route is between about 0.5 mg and about 3.5 mg every four hours;
(C) an initial sub-analgesic dosage, in controlled-release dosage form, for a naive human adult through a subcutaneous, intravenous, intramuscular, buccal or sublingual route is between about 1.5 mg and about 10.5 mg every 12 hours;
(D) an initial sub-analgesic dosage, in controlled-release dosage form, for a naive human adult through a subcutaneous, intravenous, intramuscular, buccal or sublingual route is between about 3.0 mg and about 21.0 mg every 24 hours;
(E) an initial sub-analgesic dosage for a naive human adult through an oral or rectal route is between about 2.0 mg and about 25.0 mg every four hours;
(F) an initial sub-analgesic dosage, in controlled-release dosage form, for a naive human adult through an oral or rectal route is between about 6.0 mg and about 75.0 mg every 12 hours;
(G) an initial sub-analgesic dosage, in controlled-release dosage form, for a naive human adult through an oral or rectal route is between about 12.0 mg and about 150.0 mg every 24 hours;
(H) an initial sub-analgesic dosage for a human child through an intracerebroventricular route is between about 0.05 mg and about 0.25 mg per day
(I) an initial sub-analgesic dosage for a naive human child through a subcutaneous route is between about 0.01 mg/kg and about 0.09 mg/kg every four hours;
(J) an initial sub-analgesic dosage of morphine for a naive human child through an intravenous route is between about 0.01 mg/kg and about 0.04 mg/kg every four hours;
(K) an initial sub-analgesic dosage for a naive human child through an oral or rectal route is between about 0.1 mg/kg and about 0.4 mg/kg every four hours;
(L) an initial sub-analgesic dosage for a naive lower animal through an oral or parenteral route is between about 0.5 mg/kg and about 5 mg/kg every three to six hours;
and a sub-analgesic dosage of oxycodone or a pharmaceutically acceptable salt thereof, wherein the dosage is selected from the group consisting of:
  (i) an initial sub-analgesic dosage for a human adult through an intracerebroventricular route is between about 0.05 mg and about 0.25 mg per day;
  (ii) an initial sub-analgesic dosage for a naive human adult through a subcutaneous or intravenous route is between about 1.0 mg and about 8.0 mg every four hours;
  (iii) an initial sub-analgesic dosage, in controlled-release dosage form, for a naive human adult through a subcutaneous or intravenous route is between about 3.0 mg and about 24.0 mg every 12 hours;
  (iv) an initial sub-analgesic dosage, in controlled-release dosage form, for a naive human adult through a subcutaneous or intravenous route is between about 6.0 mg and about 48.0 mg every 24 hours;
  (v) an initial sub-analgesic dosage for a naive human adult through an oral or rectal route is between about 1.0 mg and about 8.0 mg every four hours;
  (vi) an initial sub-analgesic dosage, in controlled-release dosage form, for a naive human adult through an oral or rectal route is between about 3.0 mg and about 24.0 mg every 12 hours;
  (vii) an initial sub-analgesic dosage, in controlled-release dosage form, for a naive human adult through an oral or rectal route is between about 6.0 mg and about 48.0 mg every 24 hours;
  (viii) an initial sub-analgesic dosage for a human child through an intracerebroventricular route is between about 0.05 mg and about 0.25 mg per day;
  (ix) an initial sub-analgesic dosage for a naive human child through a subcutaneous or intravenous route is between about 0.01 mg/kg and about 0.08 mg/kg every four hours;
  (x) an initial sub-analgesic dosage, in controlled-release dosage form, for a naive human child through a subcutaneous or intravenous route is between about 0.03 mg/kg and about 0.24 mg/kg every 12 hours;
  (xi) an initial sub-analgesic dosage, in controlled-release dosage form, for a naive human child through a subcutaneous or intravenous route is between about 0.06 mg/kg and about 0.48 mg/kg every 24 hours;
  (xii) an initial sub-analgesic dosage for a naive human child through an oral or rectal route is between about 0.01 mg/kg and about 0.08 mg/kg every four hours;
  (xiii) an initial sub-analgesic dosage, in controlled-release dosage form, for a naive human child through an oral or rectal route is between about 0.03 mg/kg and about 0.24 mg/kg every 12 hours;
  (xiv) an initial sub-analgesic dosage, in controlled-release dosage form, for a naive human child through an oral or rectal route is between about 0.06 mg/kg and about 0.48 mg/kg every 24 hours; and
  (xv) an initial sub-analgesic dosage for a naive lower animal through an oral or parenteral route is between about 0.1 mg/kg and about 5 mg/kg every three to six hours.

* * * * *